(12) United States Patent
Newbound et al.

(10) Patent No.: US 8,603,984 B2
(45) Date of Patent: Dec. 10, 2013

(54) METHODS FOR CONTROLLING PAIN IN CANINES USING A TRANSDERMAL SOLUTION OF FENTANYL

(75) Inventors: Garret Conrad Newbound, Carmel, IN (US); Terrence Patrick Clark, Cottage Grove, WI (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/368,356

(22) Filed: Feb. 8, 2012

(65) Prior Publication Data

US 2012/0208849 A1    Aug. 16, 2012

Related U.S. Application Data

(60) Provisional application No. 61/442,884, filed on Feb. 15, 2011.

(51) Int. Cl.
*A61P 25/04* (2006.01)

(52) U.S. Cl.
USPC ........... 514/18.4; 514/317; 514/349; 514/817

(58) Field of Classification Search
USPC ................................ 514/18.4, 817, 317, 349
See application file for complete search history.

(56) References Cited

U.S. PATENT DOCUMENTS

| | | |
|---|---|---|
| 6,299,900 B1 | 10/2001 | Reed et al. |
| 6,818,226 B2 | 11/2004 | Reed et al. |
| 6,916,486 B2 | 7/2005 | Klose et al. |
| 2004/0028625 A1* | 2/2004 | Klose et al. ................... 424/59 |
| 2011/0009292 A1 | 1/2011 | Ofstead et al. |

FOREIGN PATENT DOCUMENTS

| | | |
|---|---|---|
| WO | 2011/000049 | 1/2001 |
| WO | 2004/000263 A1 | 12/2003 |
| WO | 2004/000275 A1 | 12/2003 |
| WO | 2005/051476 A1 | 6/2005 |
| WO | 2009/047779 A2 | 4/2009 |
| WO | 2011/049951 A1 | 4/2011 |

OTHER PUBLICATIONS

Robinson et al., "A comparison of transdermal fentanyl versus epidural morphine for analgesia in dogs undergoing major orthopedic surgery", Mar. 1, 1999, Journal of the American Animal Hospital Association, vol. 35 No. 2, pp. 95-100.*

* cited by examiner

*Primary Examiner* — Ali Soroush
(74) *Attorney, Agent, or Firm* — James J. Sales

(57) ABSTRACT

This invention provides methods of controlling pain in a canine comprising transdermally administering a composition comprising fentanyl, a penetration enhancer, and a volatile liquid, wherein the composition is a solution. The invention also provides a single unit dose of the composition.

36 Claims, 9 Drawing Sheets

Fig. 4A  Fig. 5A  Fig. 7A
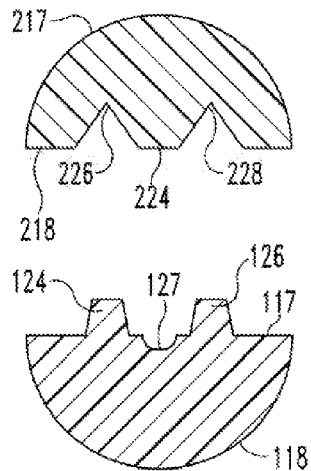 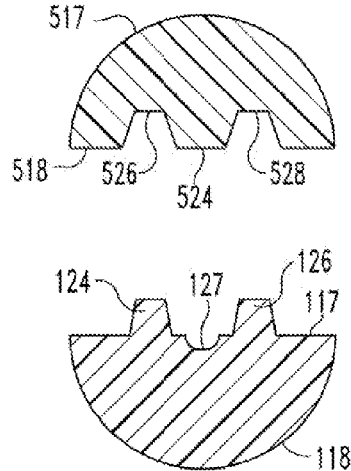 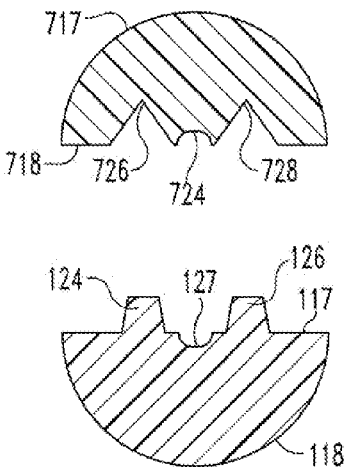
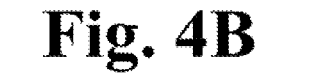  
Fig. 4B  Fig. 5B  Fig. 7B
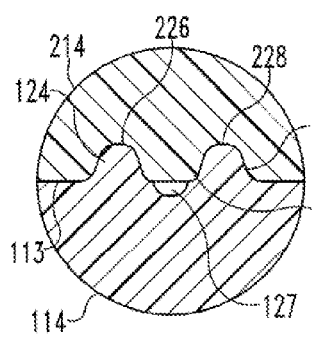 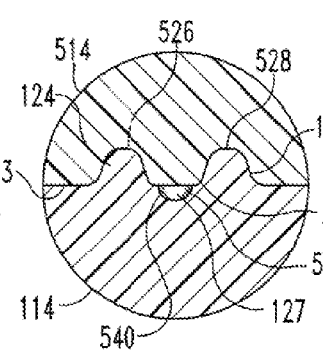 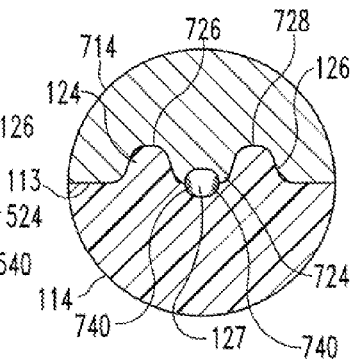
Fig. 4C  Fig. 5C  Fig. 7C

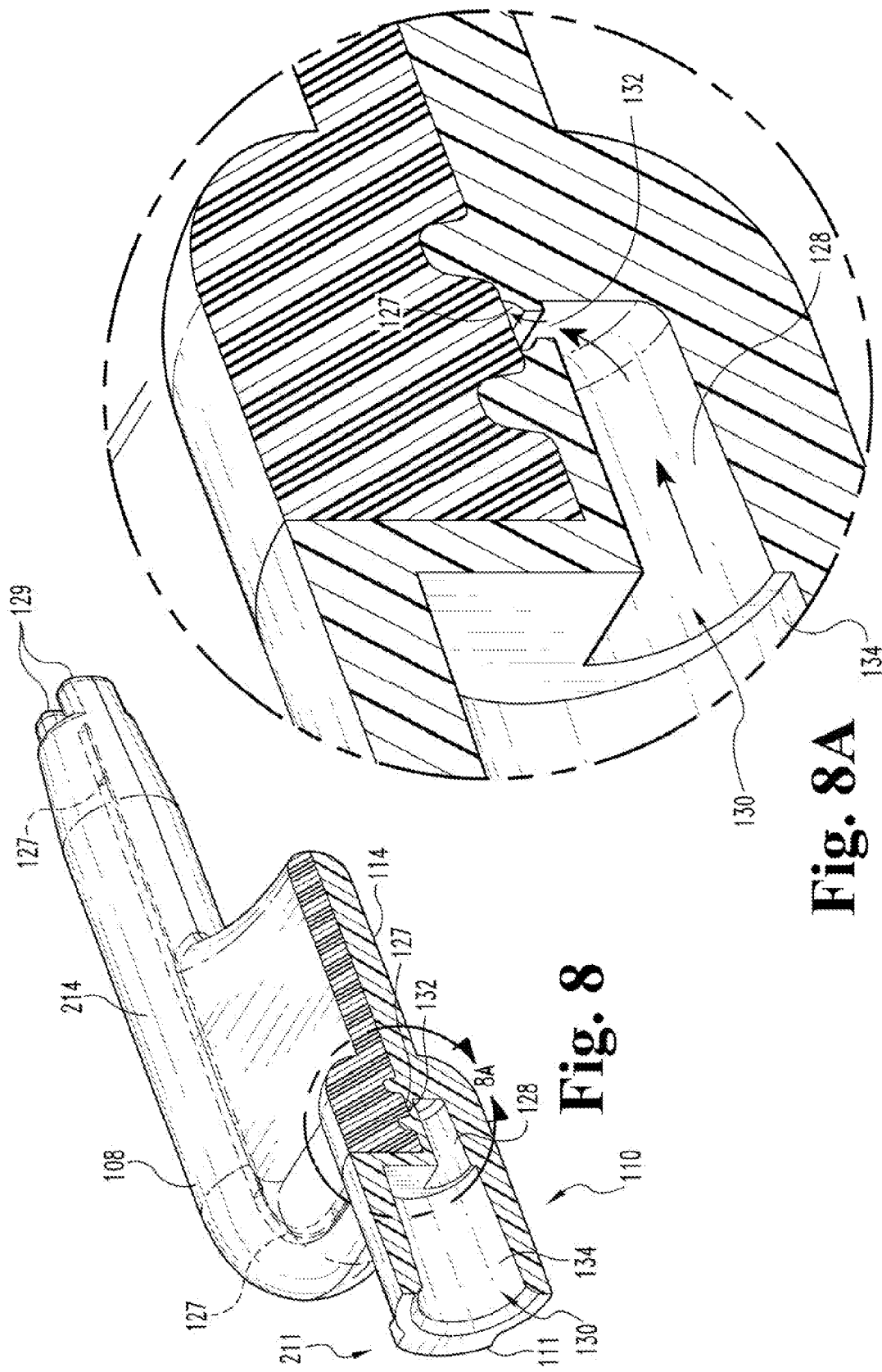

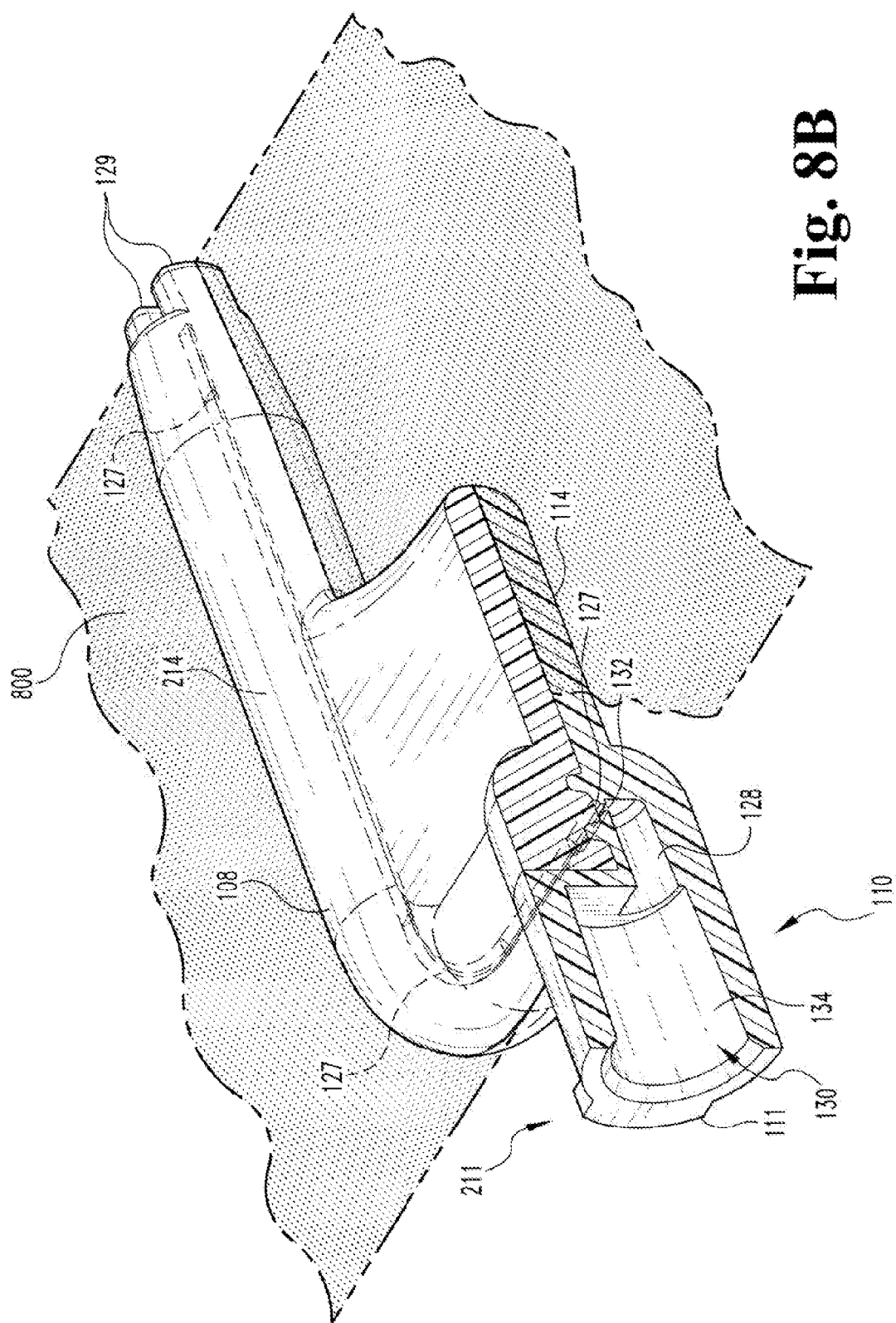

METHODS FOR CONTROLLING PAIN IN CANINES USING A TRANSDERMAL SOLUTION OF FENTANYL

CROSS REFERENCE TO RELATED APPLICATIONS

This application claims priority under 35 U.S.C. §119(e) to U.S. Provisional Application Ser. No. 61/442,884, filed on Feb. 15, 2011, and incorporated by reference herein in its entirety.

Opioids are an important part of multi-modal perioperative analgesia, especially for moderate to severe pain. In human health, the use of opioids during and after surgery for most soft tissue and orthopedic surgeries is considered as a standard of care and are included in procedure specific treatment algorithms. In veterinary medicine, the off-label use of opioids is limited by poor oral bioavailability and rapid clearance of opioids in many animals. Products currently approved by the United States Food and Drug Administration (FDA) for the control of postoperative pain in canines are essentially limited to nonsteroidal anti-inflammatory drugs (NSAIDs). Off-label opioid use in canines is primarily limited to single or repeat parenteral injections to treat acute pain or constant rate intravenous infusions and epidural or intrathecal injections delivered during anesthesia.

Fentanyl is a potent, full μ-opioid receptor agonist having approximately 100-fold the analgesic properties of the opioid morphine. However, poor oral bioavailability and rapid clearance has limited the use of fentanyl to perioperative parenteral administrations and constant rate intravenous infusions. For example, following intravenous (IV) administration of fentanyl citrate to canines, the elimination half-life and clearance has been reported to range from 0.76 to 6.0 hours and 1.7 to 4.7 L/hr·kg, respectively.

Various methods to deliver fentanyl have been attempted in order to overcome these limitations and to prolong the therapeutic duration of action. For example, methods of transdermal application such as patches have potential advantages over oral and parenteral administration, including non-invasive dosing, avoidance of the gastrointestinal tract, lack of first pass metabolism, steady, continuous drug delivery rather than a peak and trough phenomenon, potential reduction of side effects by elimination of peaks, possible reduction of lack of effectiveness due to elimination of troughs, and reduced dose frequency for convenience and increased compliance.

For extended use beyond the immediate postoperative period, transdermal delivery of fentanyl in a patch formulation has been used to treat moderate to severe pain in conscious, ambulatory canines. However, the use of fentanyl patches in canines introduces numerous additional shortcomings, including lack of regulatory approval in canines, slow onset of action, problems associated with maintaining patch contact on skin, variable fentanyl delivery rate and extent, potential inadvertent fentanyl exposure to the canine or canine owner, concern for proper control and disposal of used patches, the possibility of diversion and illicit patch use when the canine is discharged from the hospital, and lack of regulatory oversight and pharmacovigilance to track adverse events in canines.

Multiple attempts to accomplish the transdermal delivery of fentanyl without a patch have previously been unsuccessful. As a delivery method, direct drug absorption via transdermal approaches encounters the barrier nature of the skin, thus creating difficulties for most drugs to be delivered in this manner. For example, topical administration of fentanyl in a pluronic lecithin organogel did not result in measurable plasma concentration in canines.

Therefore, there exists a need for a method to use fentanyl that overcomes the limitations of parenterally-, orally-, or patch-delivered opioids in order to benefit pain management in veterinary medicine. Accordingly, the present invention provides methods of using a transdermal pharmaceutical formulation of fentanyl which exhibits desirable properties and provides related advantages for the control of pain in canines.

The present invention demonstrates that the dermal barrier to drug permeation can be overcome in canines by using a transdermal pharmaceutical formulation comprising fentanyl, a penetration enhancer, and an evaporating solvent. Through deposition of fentanyl in the stratum corneum of a canine followed by prolonged systemic absorption, the present invention overcomes the limitations of poor oral bioavailability as well as the short duration of action of orally and parenterally administered fentanyl.

BRIEF DESCRIPTION OF DRAWINGS

The teachings of some embodiments of the present invention will be better understood by reference to the description taken in conjunction with the accompanying drawings, wherein:

FIG. 4A is a cross-sectional view of the top section of an applicator of FIG. 5 taken along line 5A;

FIG. 4B is a cross-sectional view of the bottom section of an applicator of FIG. 4 taken along line 4B;

FIG. 4C is a cross-sectional view of the assembled applicator of FIG. 2 taken along line 4C;

FIG. 5A is a cross-sectional view of a different embodiment of a top section of an applicator;

FIG. 5B is a cross-sectional view of a different embodiment of a bottom section of an applicator;

FIG. 5C is a cross-sectional view of the assembled applicator after the top section of FIG. 5A is ultrasonically welded with the bottom section of FIG. 5B;

FIG. 7A is a cross-sectional view of another embodiment of a top section of an applicator;

FIG. 7B is a cross-sectional view of another embodiment of a bottom section of an applicator;

FIG. 7C is a cross-sectional view of the assembled applicator after the top section of FIG. 7A is ultrasonically welded with the bottom section of FIG. 7B;

FIG. 8 is a cross-sectional view of an assembled applicator in accordance with some embodiments;

FIG. 8A is a magnified cross-sectional view of a portion of the assembled applicator of FIG. 8 and indicated by circle 8A; and FIG. 8B is a cross-sectional view of the assembled applicator of FIG. 8 showing a plane passing through the joint.

Figure 1:
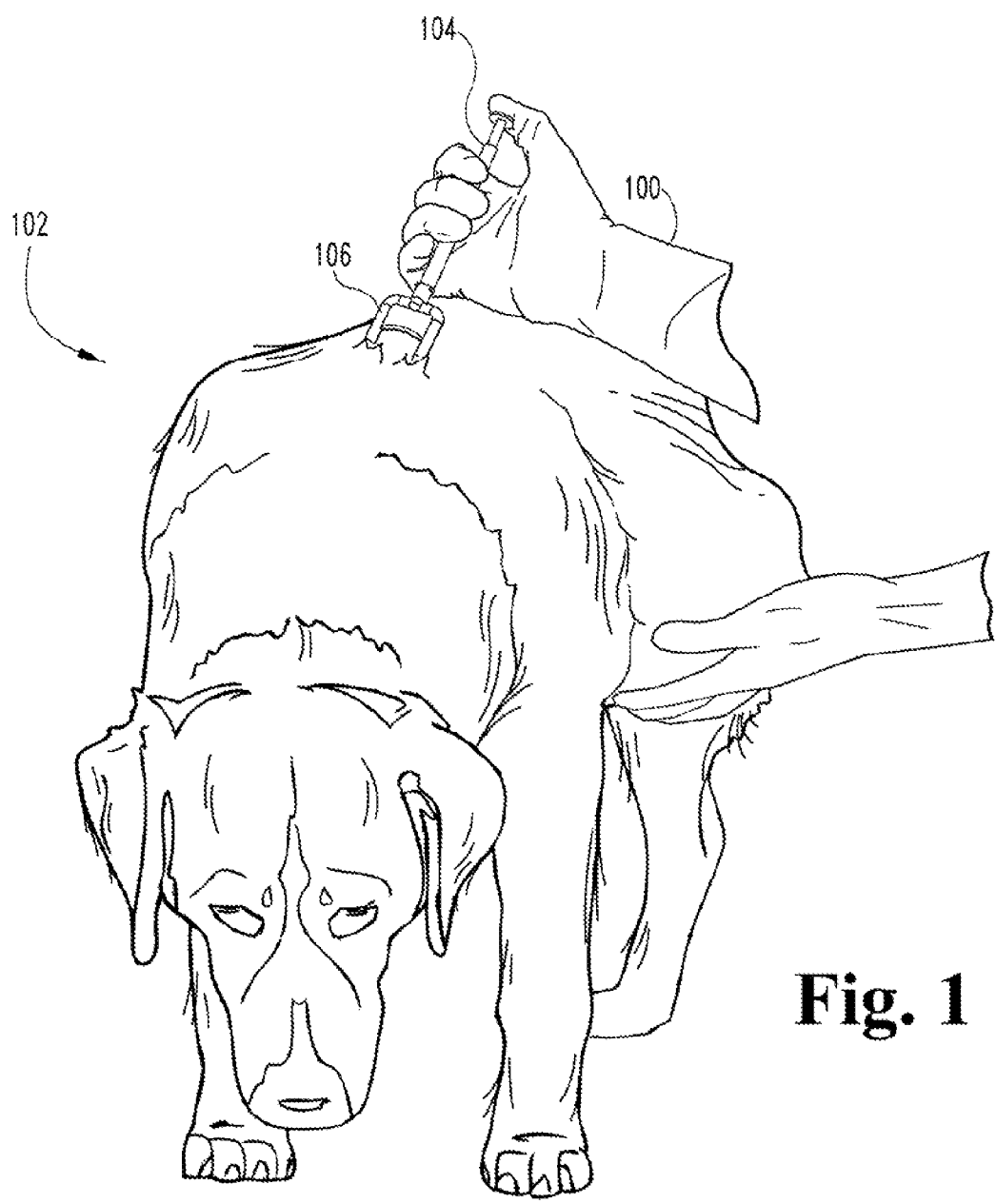
FIG. 1 is a perspective view of an assembled applicator connected to a fluid delivery device and positioned on an animal for dispensing a formulation onto the animal in accordance with some embodiments.

This invention provides methods of controlling pain in a canine comprising transdermally administering a composition comprising fentanyl, a penetration enhancer, and a volatile liquid, wherein the composition is a solution. The invention also provides a single unit dose of the composition.

The present invention provides several advantages compared to fentanyl administered to canines in a patch formulation. First, the present, invention achieves minimally effective plasma concentrations within hours of application and can be administered shortly before surgery to provide pre-emptive analgesia of a canine. Second, the present invention achieves a longer duration of action. Dependent upon the individual canine's responsiveness to fentanyl, a single dose of a therapeutically effective amount of the present invention could last several days. Third, because the present invention is a transdermal solution and not a device, the invention does not require the maintenance of skin contact in canines to maintain appropriate fentanyl absorption. Fourth, the present invention is administered on a per kilogram basis that results in dose-proportional pharmacokinetics, thus overcoming problems with variable rate and extent of fentanyl delivered to canines in a patch formulation. Fifth, the present invention limits inadvertent exposure to the canine or the canine owner because fentanyl is rapidly sequestered in the stratum cornuem immediately after drying, and no fentanyl reservoir is present. Finally, without a fentanyl reservoir, diversion and illicit use of the present invention, as well as disposal concerns outside the control of a licensed veterinarian, are minimized.

The methods according to the present invention utilize administration of a composition to a canine for control of pain. As used herein, the terms "control of pain" or "controlling pain" refer to preventing, minimizing, or eliminating pain in a canine. As used herein, the term "pain" represents all categories of pain, including traumatic pain resulting from tissue injury, post-surgical pain, burn pain, inflammatory pain, pain associated with disease (such as cancer, infection, osteoarthritis, rheumatoid arthritis, or other type of arthritis), pain associated with nerve damage, neuropathy, and other forms of neuralgic, neuropathic and idiopathic pain syndromes, and specific organ or tissue pain, such as ocular and corneal pain, bone pain, heart pain, skin pain, visceral (kidney, gall bladder, gastrointestinal, etc.) pain, joint pain, dental pain, and muscle pain. The term "pain" also includes pain of varying severity, i.e. mild, moderate and severe pain, as well as acute and chronic pain.

In some embodiments of the present invention, the methods utilize administration of a composition to a canine for control of pain during an effective period of time. As used herein, the term "effective period of time" comprises a period of at least 24 hours. In some embodiments, an effective period of time comprises a period of at least 24 hours, a period of at least 48 hours, a period of at least 72 hours, a period of at least 96 hours, or a period of at least 7 days.

The composition administered according to the present invention comprises fentanyl, a penetration enhancer, and a volatile liquid. Fentanyl is a full μ-opioid receptor agonist and is also known by chemical names such as N-Phenyl-N-[1-(2-phenylethyl)-4-piperidinyl]propanamide, N-(1-phenethyl-4-piperidyl)-propionanilide, or N-(1-phenethyl-4-piperidinyl)-N-phenylpropionamide. The chemical structure of fentanyl is:

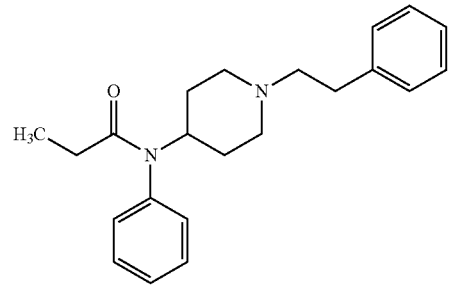 [SMILES: CCC(=O)N(c1ccccc1)C1CCN(CCc2ccccc2)CC1]

As used herein, the term "fentanyl" refers to fentanyl base, pharmaceutically acceptable salts of fentanyl, or other salts of fentanyl. The term "pharmaceutically acceptable salt" refers to an addition salt that exists in conjunction with the acidic or basic portion of fentanyl. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when fentanyl and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when fentanyl and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

As used herein, the term "penetration enhancer" refers to a chemical that improves the transport of drugs across the skin barrier. Penetration enhancers according to the present invention may act by disrupting the packing of skin lipids and thus altering the barrier nature of the stratum corneum, by changing the partitioning behavior of the drug at the stratum corneum-viable epidermis interface, or by affecting the thermodynamic activity of the drug. The penetration enhancers can be of low toxicity to the skin and are typically promoters of percutaneous absorption. In some embodiments, the penetration enhancer is a lipophilic chemical. Penetration enhancers and uses thereof are described, for example, in U.S. Pat. Nos. 6,299,900, 6,818,226, and 6,916,486.

The penetration enhancers according to the present invention are particularly suitable for transdermal delivery of analgesics through the skin of an animal such as a canine. A number of penetration enhancers are known in the art. In some embodiments, penetration enhancers include fatty acids, fatty acid esters, fatty alcohols, glycols and glycol esters, 1,3-dioxolanes and 1,3-dioxanes, macrocyclic ketones containing at least 12 carbon atoms, oxazolidinones and oxazolidinone derivatives, alkyl-2-(N,N-disubstituted amino)-alkanoate esters, (N,N-disubstituted amino)-alkanol alkanoates, sunscreen esters, and mixtures thereof. In some embodiments, penetration enhancers are selected from the group consisting of oleic acid, oleyl alcohol, cyclopentadecanone (CPE-218™), sorbitan monooleate, glycerol monooleate, propylene glycol monolaurate, polyethylene glycol monolaurate, 2-n-nonyl 1,3-dioxolane (SEPA™), dodecyl 2-(N,N-dimethylamino)-propionate (DDAIP) or its salt derivatives, 2-ethylhexyl 2-ethylhexanoate, isopropyl myristate, dimethyl isosorbide, 4-decyloxazolidinon-2-one (SR-38™, TCPI, Inc.), 3-methyl-4-decyloxazolidinon-2-one, octyl dimethyl-para-aminobenzoate, octyl para-methoxycinnamate, octisalate, and mixtures thereof.

In some embodiments, penetration enhancers can be sunscreen esters such as the compounds described in U.S. Pat. No. 6,299,900. For example, the compounds can be safe skin-tolerant ester sunscreens of formula:

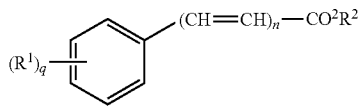

wherein $R^1$ is hydrogen, lower alkyl, lower alkoxy, halide, hydroxy or $NR^3R^4$;
$R.sup.^2$ is long chain alkyl;
$R^3$ and $R^4$ are each independently hydrogen, lower alkyl or $R^3$ and $R^4$ together with the nitrogen atom to which they are attached form a 5- or 6-membered heterocyclic ring;
n is 0 or 1; and
q is 1 or 2.

In some embodiments, penetration enhancers are esters having a long chain alkyl para-aminobenzoate, long chain alkyl dimethyl-para-aminobenzoate, long chain alkyl cinnamate, long chain alkyl methoxycinnamate or long chain alkyl salicylate. In some embodiments, penetration enhancers are selected from the group consisting of octyl dimethyl-para-aminobenzoate ("Padimate O"), octyl para-methoxycinnamate, octyl salicylate (also known as octisalate) or mixtures thereof, In one embodiment, the penetration enhancer is octyl salicylate.

As used herein, the term "volatile liquid" refers to any pharmacologically suitable liquid composition known in the art. For example, a volatile liquid may be readily vaporizable at low temperatures or tends to evaporate rapidly. Once applied to the skin, rapid evaporation of volatile liquids according to the present invention can result in super-saturation of other ingredients of the composition. In some embodiments, volatile liquids according to the present invention include safe skin-tolerant solvents. In some embodiments, the volatile liquid is a lower alkyl alcohol or a mixture of such alcohols. In some embodiments, the volatile liquid selected from the group consisting of ethanol, ethyl acetate, isopropanol, acetone, ethyl formate, methanol, methyl acetate, methyl ethyl ketone, pentan, chloroform, or mixtures thereof. In other embodiments, the volatile liquid is ethanol or isopropanol or mixtures thereof. In one embodiment, the volatile liquid is isopropanol.

The methods according to the present invention utilize administration of a composition wherein the composition is in a solution. In some embodiments of the present invention, the composition comprises fentanyl, a penetration enhancer, and a volatile liquid at various amounts based on a weight per volume of the solution. In some embodiments, the composition comprises on a weight basis from about 0.1 to about 10% of fentanyl, from about 0.1 to about 10% of the penetration enhancer, and from about 80% to about 99.8% of the volatile liquid. In another embodiment, the composition comprises on a weight basis from about 1 to about 10% of fentanyl, from about 1 to about 10% of the penetration enhancer, and from about 80% to about 98% of the volatile liquid. In another embodiment, the composition comprises on a weight basis from about 2 to about 8% of fentanyl, from about 2 to about 8% of the penetration enhancer, and from about 84% to about 96% of the volatile liquid. In another embodiment, the composition comprises on a weight basis from about 3 to about 7% of fentanyl, from about 3 to about 7% of the penetration enhancer, and from about 86% to about 94% of the volatile liquid. In yet another embodiment, the composition comprises on a weight basis from about 1 to about 5% of fentanyl, from about 1 to about 5% of the penetration enhancer, and from about 90% to about 98% of the volatile liquid. In another embodiment, the composition comprises on a weight basis about 5% of fentanyl; about 5% of the penetration enhancer, and about 90% of the volatile liquid.

Furthermore, the methods according to the present invention utilize administration of a composition wherein the administration is a transdermal administration. As used herein, the term "transdermal" has its ordinary meaning in the art and refers to passage of an agent across at least one skin layer of an animal, for example a canine. Further, the term "transdermal" is used co-terminously with the term "topical" in describing the application of agents to the skin. Both terms "topical" and "transdermal" are used herein in the broadest sense to refer to administration of a drug to the skin surface of an animal so that the drug passes through the skin layer. Unless otherwise stated or implied, the terms topical drug delivery and transdermal drug delivery are used interchangeably. From a strict drug-delivery perspective, "transdermal" is sometimes used to refer only to systemic delivery through the skin whereas "topical" requires only delivery into or on the skin for local effect. The invention described in this specification is equally applicable to both transdermal and topical modes of delivery, and is described here as "transdermal" only for convenience. The methods according to the present invention may utilize transdermal administration of the composition wherein the composition is desirably not a transdermal patch.

In carrying out the methods of this invention, the amount of fentanyl in the composition is adequate to achieve a therapeutic effect. As used herein, the term "therapeutically effective amount" refers to an amount which gives the desired benefit to a canine and includes both treatment and prophylactic administration. The amount will vary from one canine to another and will depend upon a number of factors, including the overall physical condition of the canine and the underlying cause of the condition to be treated.

The amount of fentanyl used for the controlling pain gives an acceptable rate of change and maintains desired response at a beneficial level. A therapeutically effective amount of the composition used in the methods of this invention may be readily ascertained by one of ordinary skill in the art using publicly available materials and procedures. In one embodiment of the present invention, the therapeutically effective amount of fentanyl to be delivered can be quantified by determining milligrams of fentanyl per kilogram of canine body weight. In some embodiments, the therapeutically effective amount of fentanyl in the composition can be present in an amount of between about 0.01 and about 10 milligrams per kilogram of canine body weight. In another embodiment, the therapeutically effective amount of fentanyl in the composition can be present in an amount of between about 0.1 and about 10 milligrams per kilogram of canine body weight. In yet another embodiment, the therapeutically effective amount of fentanyl in the composition can be present in an amount of between about 1 and about 5 milligrams per kilogram of canine body weight. In some embodiments, the therapeutically effective amount of fentanyl in the composition can be present in an amount of between about 2 and about 4 milligrams per kilogram of canine body weight. In some embodiments, the therapeutically effective amount of fentanyl in the composition can be present in an amount of between about 2 and about 3 milligrams per kilogram of canine body weight. In one embodiment, the therapeutically effective amount of fentanyl present in the composition is about 2.7 mg/kg. In one embodiment, the therapeutically effective amount of fentanyl present in the composition is about 2.6 mg/kg.

In one embodiment, the composition according to the present invention comprises on a weight basis about 5% of fentanyl in a solution (i.e., 50 mg/mL) and the therapeutically effective amount of fentanyl present in the composition is about 2.7 mg/kg. In this embodiment, the methods of the present invention can be transdermally administered to a canine according to the doses shown in Table 1.

TABLE 1

Doses of the Composition of the Present Invention Based on Canine Body Weight

| Pounds of body weight | Dose (mL) | Kilograms of body weight |
|---|---|---|
| 6.0 to 9.3* | 0.2 | 3.0 to 4.2 |
| 9.4 to 13.4 | 0.3 | 4.3 to 6.1 |
| 13.5 to 17.6 | 0.4 | 6.2 to 8.0 |
| 17.7 to 21.8 | 0.5 | 8.1 to 9.9 |
| 21.9 to 25.9 | 0.6 | 10.0 to 11.7 |
| 26.0 to 30.1 | 0.7 | 11.8 to 13.6 |
| 30.2 to 34.3 | 0.8 | 13.7 to 15.5 |
| 34.4 to 38.4 | 0.9 | 15.6 to 17.4 |
| 38.5 to 42.6 | 1.0 | 17.5 to 19.3 |
| 42.7 to 46.8 | 1.1 | 19.4 to 21.2 |
| 46.9 to 50.9 | 1.2 | 21.3 to 23.1 |
| 51.0 to 55.1 | 1.3 | 23.2 to 25.0 |
| 55.2 to 59.3 | 1.4 | 25.1 to 26.9 |
| 59.4 to 63.4 | 1.5 | 27.0 to 28.8 |
| 63.5 to 67.6 | 1.6 | 28.9 to 30.6 |
| 67.7 to 71.8 | 1.7 | 30.7 to 32.5 |
| 71.9 to 75.9 | 1.8 | 32.6 to 34.4 |
| 76.0 to 80.1 | 1.9 | 34.5 to 36.3 |
| 80.2 to 84.3 | 2.0 | 36.4 to 38.2 |
| 84.4 to 88.4 | 2.1 | 38.3 to 40.1 |
| 88.5 to 92.6 | 2.2 | 40.2 to 42.0 |
| 92.7 to 96.8 | 2.3 | 42.1 to 43.9 |
| 96.9 to 100.9 | 2.4 | 44.0 to 45.8 |
| 101.0 to 105.1 | 2.5 | 45.9 to 47.7 |
| 105.2 to 109.3 | 2.6 | 47.8 to 49.6 |
| 109.4 to 113.4 | 2.7 | 49.7 to 51.4 |
| 113.5 to 117.6 | 2.8 | 51.5 to 53.3 |
| 117.7 to 121.8 | 2.9 | 53.4 to 55.2 |
| 121.9 to 125.0 | 3.0 | 55.3 to 57.0 |

In some embodiments, the therapeutically effective amount is an amount sufficient to achieve a minimum effective plasma concentration (MEC). Generally, MEC has been defined as the minimum plasma concentration of an analgesic that is sufficient to prevent a patient from requesting a supplementary analgesic. The MEC of fentanyl in humans has been established in a population of adults undergoing abdominal surgery. Following surgery, fentanyl was delivered at a basal IV infusion rate of 20 µg/hr with 20 microgram on demand boluses self administered by the patient when pain became unacceptable. A blood sample collected just prior to the patient administering additional analgesia was considered the MEC. Over 48 hours, the MEC ranged from 0.23 to 1.18 ng/mL (mean 0.63 ng/mL) and remained relatively constant within individual patients over the 48-hour study period. Thus, in humans where pain was alleviated at 0.2 ng/mL this remained constant over time as well as for those where pain was alleviated with 1.18 ng/mL. This suggests a 6-fold range of minimally effective fentanyl concentrations dependent on individual responsiveness.

Canines cannot request their own supplementary analgesia, thus quantifying the true MEC remains difficult and depends on an observer making inferences from presumed pain related behaviors displayed by canines. Despite these limitations, behavior-based studies have evaluated analgesia and plasma fentanyl concentration in canines to approximate analgesia and drug concentrations. The results support the notion that the MEC in canines likely overlaps with that observed in humans. Studies in canines undergoing various surgeries have shown that fentanyl concentrations ranging from 0.4-1.28 ng/ml were effective in controlling pain. A review and analysis of all studies conducted with fentanyl patches in canines suggests that a mean plasma fentanyl concentration of 0.6 ng/ml is effective at providing analgesia.

In some embodiments of the present invention, pain is associated with a surgery performed or to be performed on the canine. In one embodiment of the present invention, the composition is administered between two to four hours prior to a surgery performed or to be performed on a canine. In one embodiment, the surgery performed or to be performed on the canine is an orthopedic surgery. As used herein, the term "orthopedic surgery" refers to a surgical procedure pertaining to the preservation or restoration of the function of the musculoskeletal system, its articulations, and associated structures.

In another embodiment, the surgery performed or to be performed on the canine is a soft tissue surgery. As used herein, the term "soft tissue surgery" refers to a surgical procedure pertaining to the preservation or restoration of the function of muscle, fat, fibrous tissue, blood vessels, or other supporting tissue of the body, for example tendons, ligaments, fascia, skin, nerves, or synovial membranes.

In another embodiment, the surgery performed or to be performed on the canine is associated with cranial cruciate rupture. In one embodiment, the surgery associated with cranial cruciate rupture is a stabilization surgery.

In one embodiment of the present invention, the composition is contained in a multiple-dose vial prior to administration. The multiple-dose vial containing the composition of the present invention can be made of glass, plastic, or other material. In some embodiments of the present invention, the composition is administered as a multiple dose regimen. In one embodiment, the multiple dose regimen is a time period of approximately 14 days. In another embodiment, the multiple dose regimen is a time period of approximately one month. In yet another embodiment, the multiple dose regimen is a time period of approximately two months. In another embodiment, the multiple dose regimen is a time period of approximately three months. In yet another embodiment, the multiple dose regimen is a time period of approximately four months.

In another embodiment of the present invention, the composition is administered as a single dose. In yet another embodiment of the present invention, the composition is administered as a single unit dose. As used herein, the term "unit dose" is a discrete amount of the composition comprising a predetermined amount of fentanyl. The amount of fentanyl is generally equal to the dosage of fentanyl which would be administered to a canine or a convenient fraction of such a dosage such as, for example, one-half or one-third of such a dosage.

According to the methods of the present invention, the terms "single dose" and "single unit dose" include embodiments wherein the composition can be transdermally administered as a single application and administered as multiple applications. In one embodiment, a single dose or single unit dose of the composition can be transdermally administered to a canine in a single application at one location on the canine's skin. In another embodiment, a single dose or single unit dose of the composition is transdermally administered to a canine in a single application at one location on the canine's skin, wherein the single application is about 0.5 mL of a solution of the composition. In one embodiment, a single dose or single unit dose of the composition can be transdermally administered to a canine in multiple applications at a single location on the canine's skin. In another embodiment, a single dose or single unit dose of the composition is transdermally administered to a canine in multiple applications at a single location on the canine's skin, wherein each application has up to about 0.5 mL of a solution of the composition. In one embodiment, a single dose or single unit dose of the composition can be transdermally administered to a canine in multiple applications at more than one location on the canine's skin. In another embodiment, a single dose or single unit dose of the composition is transdermally administered to a canine in multiple applications at more than one location on the canine's skin, wherein each application has up to about 0.5 mL of a solution of the composition. In embodiments wherein multiple applications of the composition are utilized, the multiple applications can be administered to the canine over a reasonable duration of time.

In one embodiment of the present invention, the composition is transdermally administered to a canine at a dorsal location of the canine. According to the methods of the present invention, the term "dorsal" has its ordinary meaning and as used herein refers to the direction to the rear of the spine of a canine, i.e., outwardly through the canine's back. In one embodiment of the present invention, the composition is transdermally administered to a canine at a ventral location of the canine. According to the methods of the present invention, the term "ventral" has its ordinary meaning and as used herein refers to the direction to the front of the spine of a canine, i.e., frontwards through the canine's body.

The compositions of the present invention include those that also optionally contain one or more other active ingredients, in addition to fentanyl. As used herein, the term "active ingredient" or "therapeutic ingredient" refers to a therapeutically active compound, as well as any prodrugs thereof and pharmaceutically acceptable salts, hydrates, and solvates of the compound and the prodrugs. Other active ingredients may be combined with fentanyl and may be either administered separately or in the same pharmaceutical formulation. The amount of other active ingredients to be given may be readily determined by one skilled in the art based upon therapy with fentanyl.

In one embodiment of the methods according to the present invention, a transdermal dispensing apparatus can be used to administer the composition to a canine. In one embodiment, the transdermal dispensing apparatus is an applicator for dispensing a formulation herein described to an animal. An example of a transdermal dispensing apparatus is described, for example, in PCT Patent Application No. PCT/US2010/053206 and in U.S. patent application Ser. No. 12/581,658.

The applicator comprises a housing including first and second sections coupled together, the first and second sections defining a channel therebetween that includes at least one outlet; a hub integral with the first section and extending therefrom, the hub defining a conduit; and a bent path connecting the conduit to the channel. In accordance with this embodiment, the conduit, the bent path and the channel are fluidly connected.

In accordance with still another aspect of the present invention, a method is provided for dispensing the formulation herein described from an applicator of the type having a housing including first and second sections coupled together to form a channel and a hub extending from the housing, the hub being attachable to a syringe. The method comprises attaching the hub to a syringe containing a formulation; placing an outlet of the applicator on or near the animal; causing the formulation to be released from the syringe into the applicator; passing the formulation through the hub, through a bent path and then into the channel; and dispensing the formulation from the applicator through the outlet.

The applicators described herein can be particularly useful for transdermally delivering doses of controlled veterinary substances (e.g., fentanyl) to the coat and skin of an animal, which may include a canine. In certain exemplary embodiments, the drug delivery device includes an applicator device or tip that is compatible with a standard luer lock syringe and consists of a housing that allows the formulation to be spread over a surface area of the animal's skin or coat. To accomplish this, the applicator body includes one or more outlets that are in the form of legs or tines configured to penetrate the fur of the animal and thereby deliver the drug directly to the animal's skin or coat. In certain aspects, the outlet(s) further includes a pair of spaced prongs or feet that extend from its distal end, thereby allowing the formulation to be freely dispensed onto the surface of the animal. More particularly, because the spaced feet extend outwardly from the distal end of applicator, they are the only structural portion of the assembled applicator that directly contact and seal against the surface of the animal. Moreover, since the outlet opening is positioned between the spaced apart prongs and in such a manner that it does not directly contact or seal against the surface of the animal during a dispensing operation, the formulation is able to be freely dispensed and spread onto the animal without being physically impeded or interrupted.

A non-limiting illustration of an assembled applicator coupled to a fluid delivery device in accordance with the present teachings is shown in FIG. 1. More specifically, FIG. 1 depicts a perspective view of a user 100 dispensing a formulation herein described onto an animal 102. In accordance with this exemplary and non-limiting illustration, a fluid delivery device 104 containing the formulation is releasably attached to an applicator device 106 and then placed on or near the surface of the animal 102. While this illustrative embodiment shows the fluid delivery device 104 as a standard syringe, it should be understood and appreciated herein that delivery of the formulation may be accomplished by any known fluid delivery device or connector that is releasably attachable to the applicator device 106 and having a reservoir for holding and/or storing the formulation to be dosed or dispensed. Other such non-limiting and illustrative fluid delivery devices that may also be used include, but are not limited to, syringes, catheters, hubbed needles, IV tubes and cylinder fluid delivery devices.

As will be explained in detail below, the applicator devices 106 generally consist of at least two parts or halves (i.e., sections 114 and 214) that are coupled or assembled together to form the applicator structure. Unlike many other traditional applicator devices that consist of either one applicator part or two structurally complementary parts, the devices include two sections 114, 214 that are somewhat complementary in terms of structure, yet specifically shaped in such a manner that once assembled, the formulation can be dispensed therefrom without experiencing much associated leakage or residual buildup. More particularly, the sections 114, 214 are structurally shaped such that when they are coupled together, the formulation is discouraged from leaking out of the applicator body. In addition, the structural orientation of the dispensing passageway that is created between the first and second sections is shaped in such a manner that substantially all of the formulation is encouraged from being dispensed from the applicator device during a dispensing operation. As such, it should be understood and appreciated herein that at least some of the unexpected advantages are influenced by the resultant shape and configuration of the dispensing passageway that is formed by the assembled applicator sections.

Figure 2:
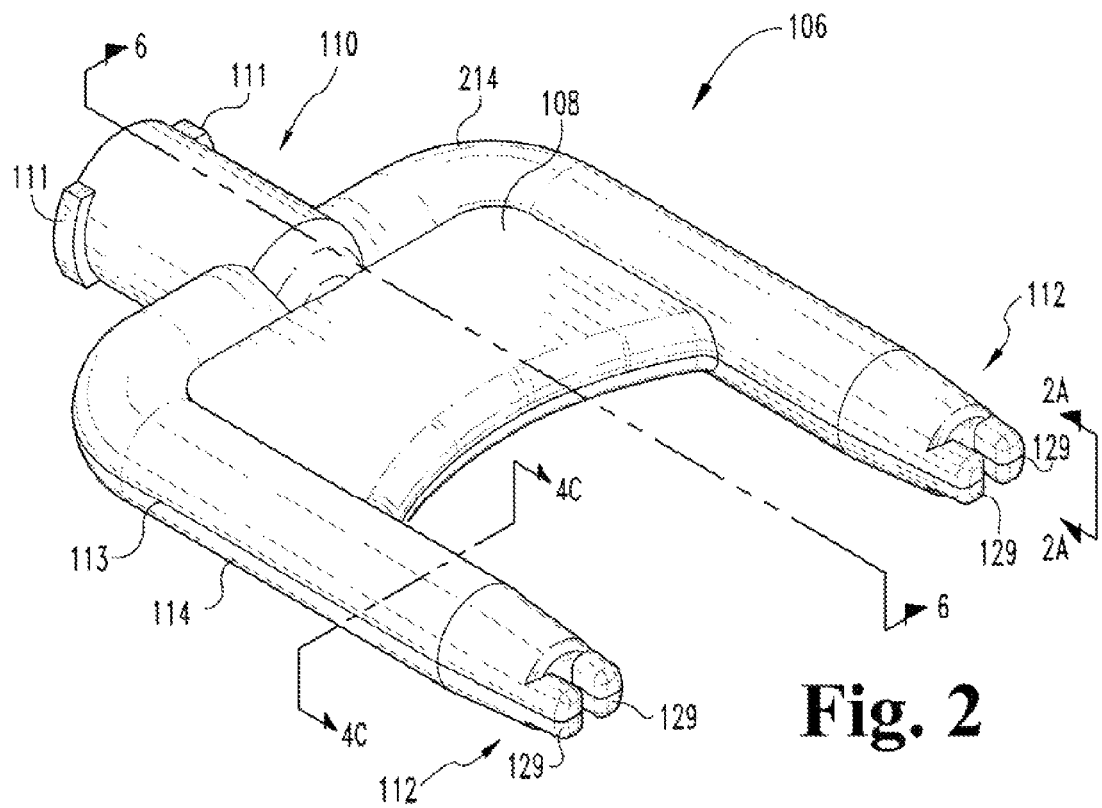
FIG. 2 is a perspective view an assembled applicator in accordance with some embodiments.

Moving now to FIG. 2 a perspective view of a fully assembled applicator 106 is shown. The applicator 106 includes a housing or body 108 defining an inlet hub 110 and an outlet 112. As will be explained in more detail below, the inlet hub 110 is attachable to the drug delivery device 104 during a dispensing operation, whereas the outlet portion 112 is capable of penetrating the fur of an animal so that the formulation can be appropriately dispensed therefrom and onto the surface of the animal. The applicator 106 can be made from polyethylene, polypropylene, polyvinyl acetate, polystyrene, polyethylene terephthalate, polybutylene terephthalate, and polytetrafluoroethylene, and the like.

Figure 3:
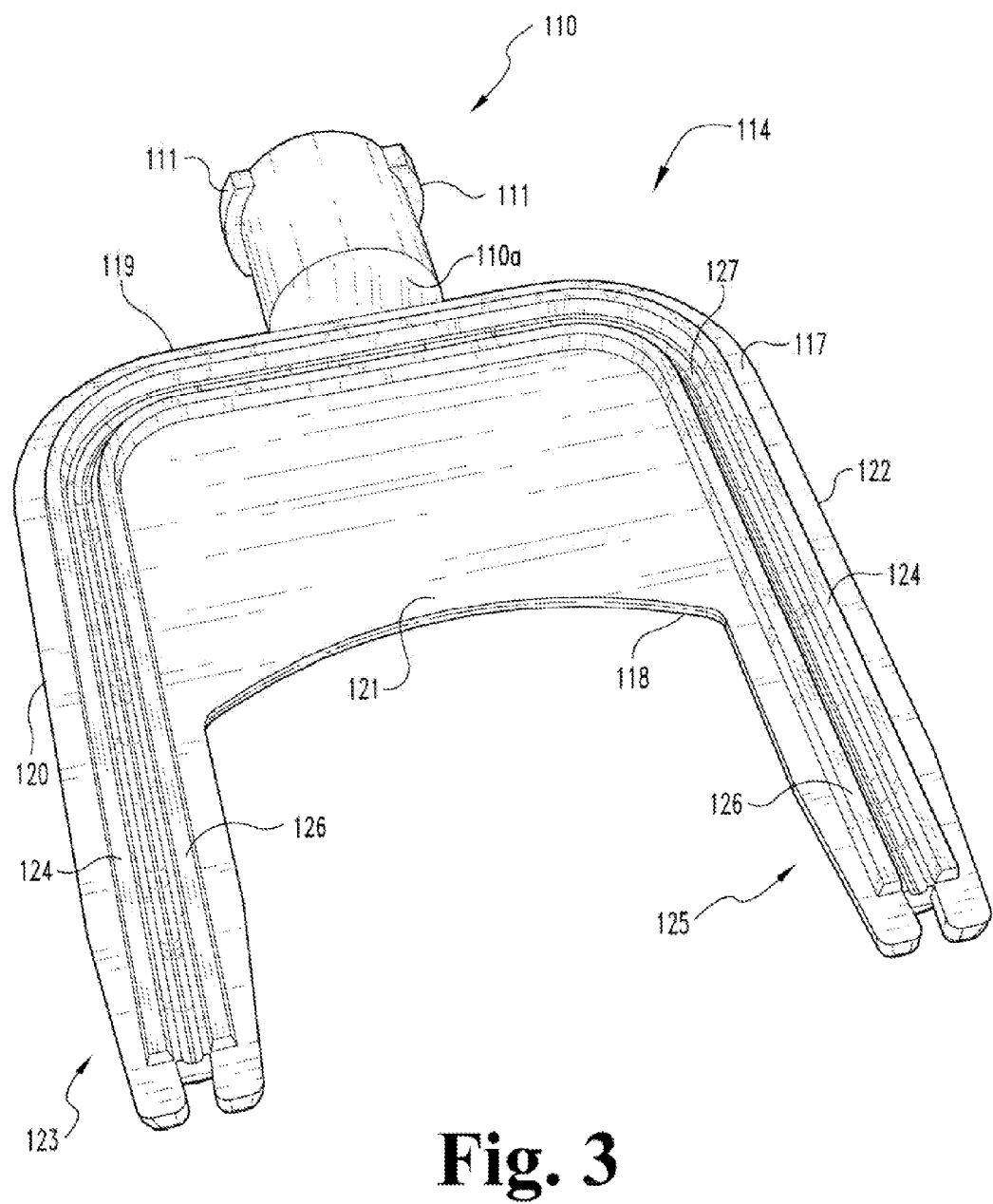
FIG. 3 is a perspective view of the bottom section of an applicator in accordance with some embodiments.
Figure 4:
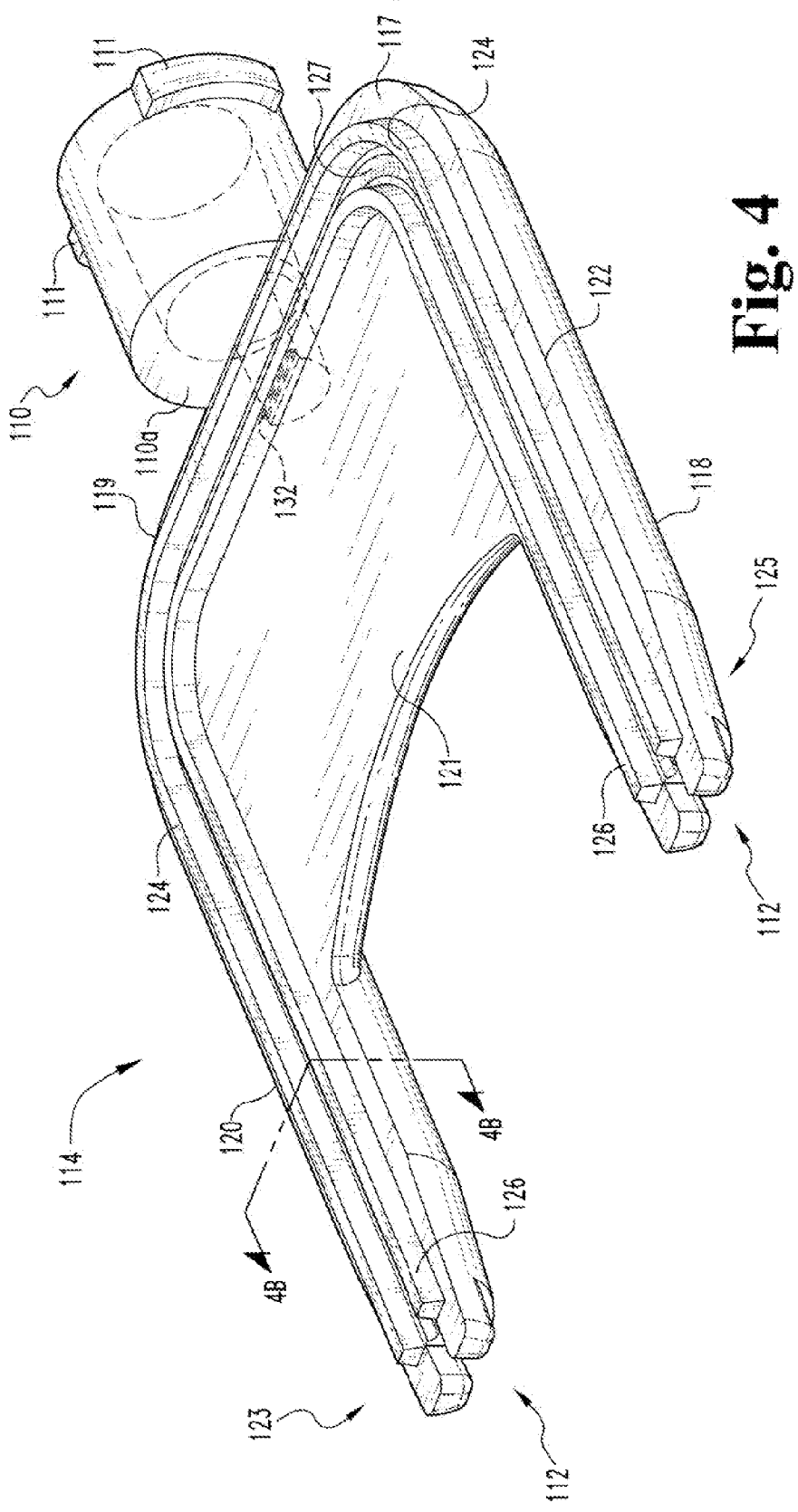
FIG. 4 is another perspective view of the bottom section of an applicator in accordance with some embodiments.

In terms of assembly, the applicator 106 comprises first and second sections or faces (114, 214) that are coupled or assembled together to form the housing 108. As shown in FIGS. 3 and 4, the first section 114 includes a top surface 117, a bottom surface 118, a back edge 119 integral with the inlet hub 110 and first and second sides 120, 122, the first and second sides being defined by a pair of substantially parallel outlet ends or legs 123, 125 that extend from and partially surround a substantially flat middle section 121 that is disposed between the first and second sides 120, 122. Extending upwardly from the top surface 117 of the first preassembled section 114 and positioned substantially along its outer periphery are a pair of ribs 124, 126 that are spaced from each other in a parallel fashion. In certain exemplary embodiments, the ribs 124, 126 are trapezoidal shaped and have four sides with the top and bottom sides being parallel to one another. In accordance with this exemplary embodiment, the spaced ribs 124, 126 have a groove or channel 127 that is formed therebetween.

In certain aspects, the groove 127 is sunken or depressed below the top surface 117 of the first section, thereby creating a channel for delivering the formulation to the outlet ends 123, 125 and ultimately onto the animal. To achieve the sunken channel formation, the groove 127 is provided as a depression below the surface 117 and has a substantially semi-circular shape. A more detailed and non-limiting exemplary illustration of this semi-circular geometry can be seen with reference to FIG. 4B, which illustrates a cross-sectional view of the first section 114 taken along line 4B of FIG. 4. While this exemplary illustration shows the groove or channel 127 being semi-circular in shape, it should be understood and appreciated herein that any known geometric shape useful for establishing a channel that permits a fluid or other such liquid agent to travel therethrough is envisioned and can be used.

As explained above, it should be understood and appreciated herein that the first preassembled section 114 is configured to be coupled to and molded with the second preassembled section 214 to form a fully assembled applicator device 106. In addition, the channel or groove 127 that is formed between the ribs 124 and 126 is positioned and shaped in such a manner that a fluid passageway or conduit for dispensing the formulation is formed between the fluid delivery device 104 and the dispensing end of the outlet 112 once section 114 is coupled to and molded with section 214.

Figure 5:
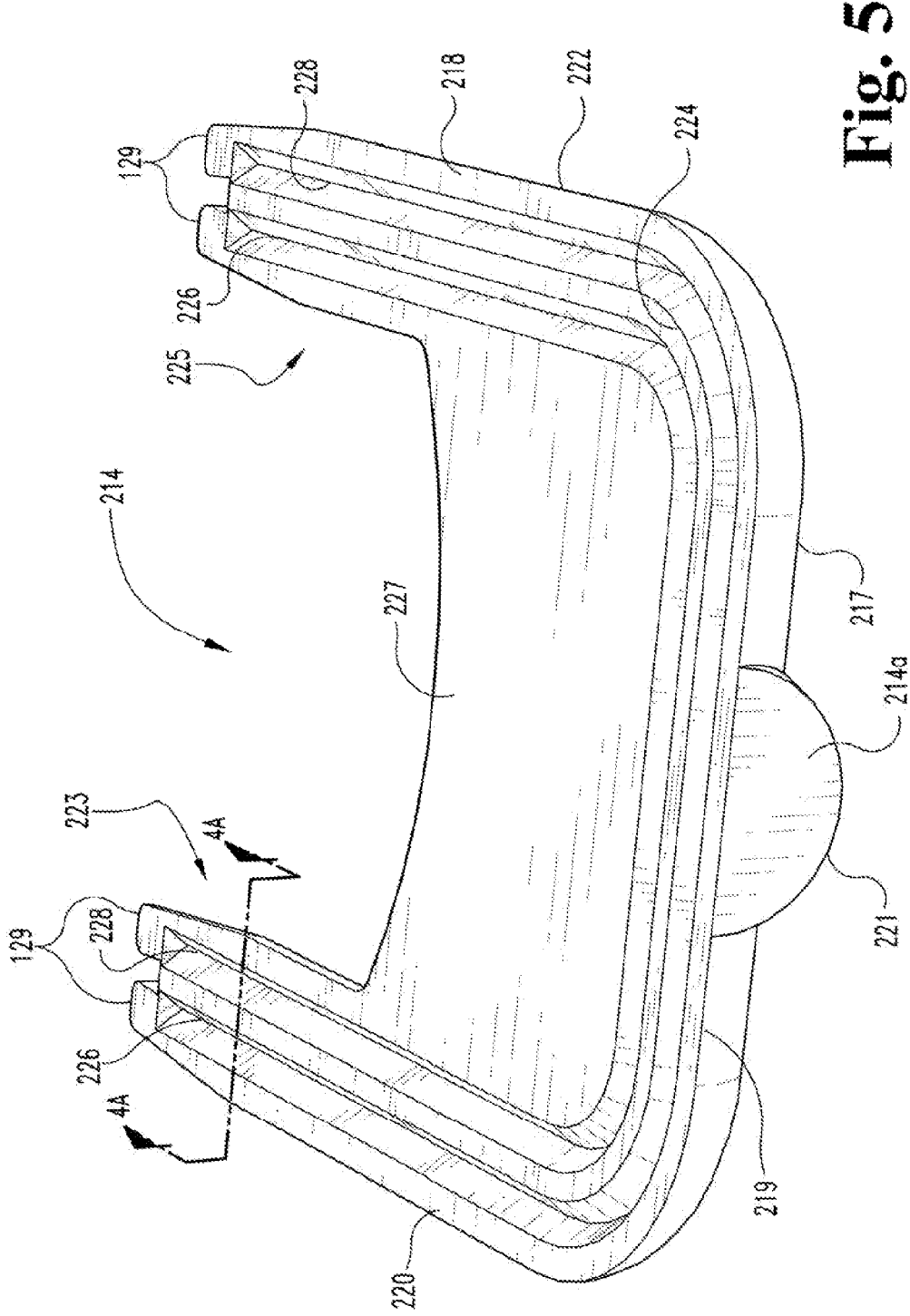
FIG. 5 is a perspective view of the top section of an applicator in accordance with some embodiments.

Moving now to FIG. 5, the second preassembled section 214 has a shape that is substantially similar to and which complements the first preassembled section 114; however, it does not have a corresponding inlet hub portion or a rib and groove arrangement like that of the first section 114. Instead, the second section 214 includes a top surface 217, a bottom surface 218, and a back edge 219 having a rounded portion 221 that is substantially centrally located along the back edge 219 and is configured to substantially align with the inlet hub 110 portion of the first section during assembly. To achieve this alignment, the inlet hub 110 has a flat end portion 110a that is complementarily shaped to and configured to seamlessly mate with a flat end portion 214a of the second section 214. The second preassembled section 214 also includes first and second sides 220, 222 that are defined by a pair of substantially parallel outlet ends or legs 223, 225 that extend from and partially surround a substantially flat middle section 227 that is disposed between the first and second sides 220, 222. Extending outwardly from the bottom surface 218 of the second section and positioned substantially along its outer periphery is a ledge or energy director 224 that is formed by a pair of spaced grooves 226, 228. A more detailed and non-limiting exemplary illustration of this geometric configuration can be seen with reference to FIG. 4A, which illustrates a cross-sectional view of the second section 214 taken along line 4A of FIG. 5.

Figure 6:
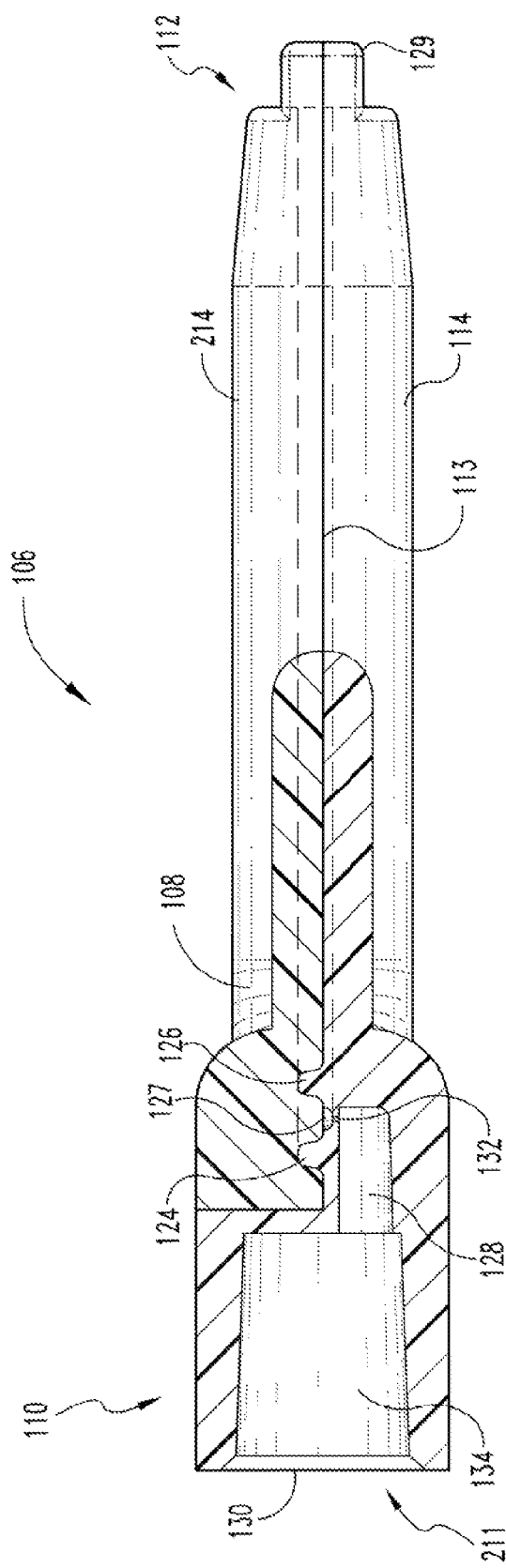
FIG. 6 is a cross-sectional side view of an assembled applicator of FIG. 2 taken along line 6.

During assembly of the applicator 106, the pair of spaced ribs 124, 126 of the first preassembled section 114 are configured to substantially align with (and mate) the spaced grooves 226, 228 of the second section 214, thereby forming the passageway or channel 127 for dispensing the formulation. In accordance with certain exemplary embodiments, the passageway 127 is asymmetric relative to a seamless joint 113 that attaches the first and second sections 114, 214 together. A fully assembled view of the first and second sections 114, 214 aligned and mated together can be seen in FIGS. 4C and 6, which respectively depict a cross-sectional view of the assembled applicator 106 from FIG. 2 taken along line 4C and a cross-sectional side view of the assembled applicator 106 from FIG. 2 taken along line 6.

Figure 2A:
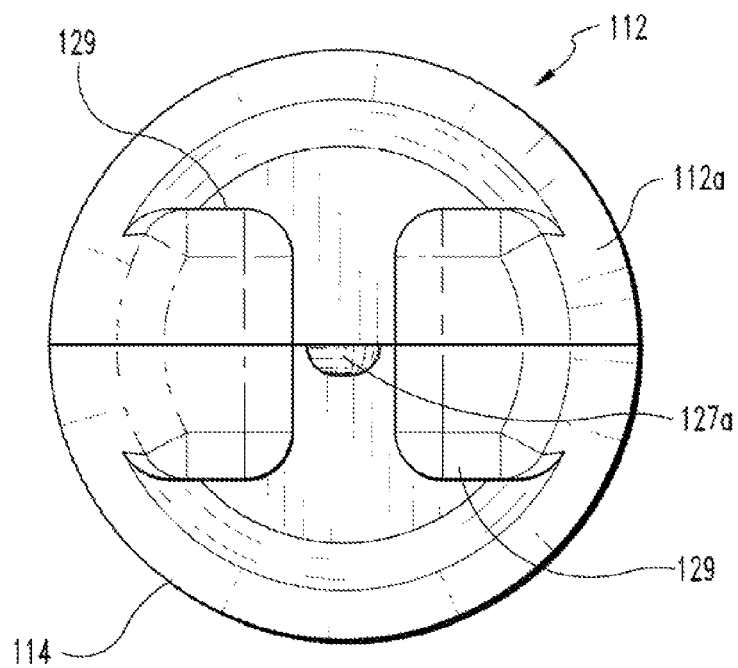
FIG. 2A is an end view of an outlet from the assembled applicator of FIG. 2 taken along line 2A.

As can be seen particularly in FIG. 4C, after the first and second sections are welded together, the spaced ribs 124, 126 meld into grooves 226, 228 so that a seamless joint 113 is formed between the two faces 114, 214, and the channel 127 is formed therebetween. In particular, a substantially flat portion of the channel 127 is defined by the seamless joint 113. Once fully assembled, the channel 127 creates a fluid passageway between the inlet hub 110 and the one or more outlets 112. As shown in FIG. 2A, the distal end 112a of the applicator's outlet is open (see reference numeral 127a) so the formulation can be emptied from channel 127 during a dispensing application.

In another embodiment, the first and second preassembled sections 114, 214 can be coupled together to form an assembled applicator 106 by various known plastic molding and manufacturing methods. However, in certain aspects, the applicator 106 is formed by ultrasonically welding the first and second preassembled sections 114, 214 together. In accordance with this exemplary and non-limiting embodiment, the first and second preassembled sections 114, 214 are mated and aligned together as explained above, and an ultrasonic weld, for instance along the ledge 224, is initiated to thereby cause the sections to seamlessly meld or join together. As is readily known and appreciated by those of skill in the plastics manufacturing and welding arts, the process of ultrasonically welding two plastic parts together along an energy director that has been formed into one of the preassembled parts allows a bond to be formed that is tensile and resists the tendency of forces to tear the bond apart. Specifically, the ultrasonic energy melts the point contact between the parts, thereby creating a seamless joint. Moreover, these types of welds can typically be strengthened by either increasing the weld depth, or increasing the size of the energy director to provide a larger weld area. Accordingly, it should be understood and appreciated herein that the precise shapes and sizes of the preassembled components described herein are not essential, particularly as a skilled artisan would understand how to maximize the size and shapes of the components to achieve the best welded result for the specific dispensing applicator device to be assembled.

There are, however, advantages to the embodiment of the applicator 106 illustrated in FIGS. 4A, 4B, and 4C. In particular, the structure of the first section 114 and second section 214 is advantageous in forming a substantially semi-circular channel 127 that encourages a formulation to be dispensed therethrough while leaving only a minimal amount of residual remaining in the channel after use. One reason for this is because the weld path, i.e., seamless joint 113, is disposed close to the fluid path, i.e., channel 127. Another reason is because the channel 127 has a substantially flat portion, the ribs 124, 126 can be positioned closer to one another. As such, the channel 127 can be smaller thereby reducing the overall volume of the channel, which effectively reduces the amount of residual formulation remaining in the channel after dispensing the agent therethrough.

Another advantage with the illustrated embodiment of the applicator 106 is the shape of the grooves 226, 228 and the ledge 224 in the second section 214. Each groove is substantially V-shaped and the ledge 224 is substantially flat, as shown in FIG. 4A, such that when the first and second preassembled sections 114, 214 are mated and aligned together there is very little, if any, flash remaining in the channel 127. During ultrasonic welding, for example, the ultrasonic energy melts the energy director, i.e., ledge 224, to form the joint 113 between the first and second sections 114, 214. In FIG. 4C, after the first section 114 and second section 214 are welded together, the channel 127 is formed without flash forming in the channel. Flash can disrupt or obstruct the flow of the formulation passing through the channel 127. Larger amounts of residual fluid can remain in the channel after the formulation is dispensed when flash is present in the channel 127. By reducing or eliminating flash, the channel 127 maintains a substantially semi-circular shape therethrough, which as described above reduces the amount of residual formulation remaining in the channel after use.

This is not, however, the case with differently shaped grooves and/or ledge in the second section. In FIG. 5A, for example, a different embodiment of a second section 514 having a top surface 517 and bottom surface 518 is shown. In addition, a different cross-section of the second section 514 is illustrated in which grooves 526, 528 are trapezoidal. The trapezoidal grooves 526, 528 are complementary to the trapezoidal ribs 124, 126 of the first section 114 (FIG. 58). An energy director or ledge 524 of the second section 514 is substantially flat and therefore similar to the ledge 224 in FIG. 4A. As can be seen in FIG. 5C, after the first and second sections are welded together, the spaced ribs 124, 126 meld into grooves 526, 528 so that a seamless joint 113 is formed between the two faces 117, 518, and the channel 127 is formed therebetween. Unlike the semi-circular channel 127 shown in FIG. 4C, however, the mating of the trapezoidal grooves 526, 528 with the trapezoidal ribs 126, 128 produces flash 540 which fills a portion of the channel 127. The flash 540 reduces the size of the channel 127 such that the channel 127 no longer is semi-circular. One reason flash is produced in the channel is due to the difficulty of welding the trapezoidal grooves 526, 528 and the trapezoidal ribs 126, 128.

In FIG. 7A, another embodiment of a second section 714 having a top surface 717 and bottom surface 718 is shown. Moreover, the second section 714 includes grooves 726, 728 which are V-shaped and therefore similar to the grooves 226, 228 of FIG. 4A. The second section 714, however, also includes an energy director or ledge 724 that is not flat. Instead, the ledge 724 is pressed above the bottom surface 718 and has a semi-circular cross-section. The shape of the ledge 724 complementarily corresponds with the semi-circular channel 127 of the first section 114 shown in FIG. 7B. As can be seen in FIG. 7C, as the first and second sections are welded together, the spaced ribs 124, 126 meld into grooves 726, 728 so that a seamless joint 113 is formed between the two faces 117, 718, and the channel is formed therebetween. The channel 127 formed between the first and second sections has a substantially circular cross-section, but flash 740 forms in the channel thereby inhibiting flow therethrough. Flash is produced in the channel 127 due to the difficulty of welding the two sections together. As can be seen in FIG. 7A, for example, the ledge 724 is no longer substantially flat. In particular, there is very little material along the ledge 724 that contacts the first section 114 for ultrasonically welding the two sections together. Thus, to ensure a proper bond is formed to hold the first and second sections together, flash fills along the edges of the channel 127. Therefore, while it should be understood and appreciated herein that the precise shapes and sizes of the preassembled components described herein are not essential, it is advantageous for the preassembled components to comprise shapes and sizes that facilitate little to no flash.

A more detailed description of the various parts of the applicator 106 will now be provided. As is particularly shown in FIGS. 6, 8, 8A and 8B, the inlet hub 110 is fluidly connected to the first section 114 by way of a path 128 that is disposed between a pair of openings 130, 132. As should be understood and appreciated herein, the fluid connection between the inlet hub 110 and the first section 114 defines a conduit for receiving the formulation from the fluid delivery device 104 to the groove or channel 127. More particularly, the inlet hub 110 has a first opening 130 that is disposed at the proximal, end 211 of the inlet hub 110 and functions as an insertion hole for receiving the dispensing end of the fluid delivery device (such as device 104 in FIG. 1). Opposite the first opening 130 is a second opening 132, which is fluidly connected to the groove or channel 127 of the housing 108. As such, the inlet hub 110 is designed to functionally form an opening for the fluid delivery device 104 so that the formulation can be easily and conveniently dispensed therefrom.

The inlet hub 110 has a pair of winged ears 111 adapted to lock to the fluid delivery device (not shown). More particularly, the fluid delivery device (e.g., device 104 in FIG. 1) is inserted into first opening 130 and securely attached to inlet hub 110 by any fastening means known in the art. Exemplary connection means include, but are not limited to, luer lock connections. Luer lock connections are well known in the field of medicine and are typically used for coupling a syringe or other such liquid or gas source to a catheter line or medical device. Moreover, as will be appreciated and understood by those skilled within the relevant art, the luer connectors may be female or male in orientation and may function as luer-locking devices, luer-slip connection devices or the like. In accordance with some specific aspects, the luer lock connection is achieved between the fluid delivery device 104 and the winged ears 111 of the inlet hub 110.

As can be appreciated from the discussion above, the flow path 128 undergoes a significant reduction in diameter along the direction of fluid flow (i.e., from the inlet hub 110 to the distal end 112*a* of the outlet 112). This is necessary to adapt the applicator for connection to larger fluid delivery devices at the end of hub 110 on the one hand, and on the other hand to the very small channel 127 through which the fluid is moved before being dispensed from the outlet(s) 112. This reduction in diameter causes significant pressure within path 128, which in turn can cause leakage if there are any weak or vulnerable points such as weld seams along path 128. To address these structural issues, path 128 is bent or shaped such that it is circuitous in nature—i.e., is not a direct route between the first and second openings 130, 132 and changes direction one or more times. In this manner, path 128 is formed entirely within a single section, section 114, of the applicator, which avoids weld seams being present for any of the structure that defines path 128. With reference to FIG. 8B, for example, the interface between the first and second sections, i.e., joint 113 (FIG. 2), defines a plane 800 that passes therethrough. As shown in this illustrative embodiment, the path 128 is offset from the plane 800. By locating the flow path in one section of the applicator (as opposed to two sections defining a flow path therebetween) and consequently eliminating all weld seams within the area defined by the flow path 128, the occurrence of leakage as the fluid flows between the fluid delivery device 104 and the channel 127 is substantially reduced, if not eliminated.

The structure defining path 128 can be appreciated with reference to FIGS. 8 and 8A, wherein the conduit defined by the inlet hub 110 includes a short hollow cylindrical chamber 134 that is disposed between the first and second openings 130, 132 and terminates substantially centrally into the channel 127 at the second opening 132. Chamber 134 is typically designed such that it is dimensionally non-uniform (i.e., varies in width and height between the first opening 130 and the second opening 132). According to this aspect, the internal diameter of the chamber 134 changes to achieve the reduction in diameter and configuration needed to maintain path 128 within a single section 114 of the applicator. As mentioned above; it has been found that this configuration avoids leakage of the formulation as it flows between the fluid delivery device and the channel.

In certain aspects, one or more tubes or other such enclosed tubular structures can be internally incorporated into the structural design of the present applicators. For instance, to avoid any associated leakage that may occur around the connection between the fluid delivery device and the applicator or along the joint 113 that is formed between the first and second molded sections 114, 214, one or more chambers can be internally added into the inlet hub 110 portion and/or within the formed channel 127 of the applicator body. While such additional structure can be incorporated into any of the embodiments without straying from the present teachings, it should be understood and appreciated herein that such structures are not required. More particularly, it has been found that utilizing the bent path orientation and complementary structural design of the applicator sections makes it possible to achieve a tubeless design that is not only free of manifolds, but is also capable of operating without resultant leakage.

In certain exemplary embodiments, the chamber 134 contains ridges, ledges, or other such similar structures to cause a bending configuration and stepped down diameter of the path 128. In still other aspects, the path 128 is positioned below the seamless joint 113 that is formed between the first and second sections 114, 214 and underneath the channel 127 formed therebetween.

In accordance with certain aspects, the second opening 132 directs the formulation into the channel in a direction that is substantially orthogonal to the lengthwise direction of the channel 127. Such exemplary embodiment can be seen, for instance, with reference to FIGS. 8 and 8A. While the dimensions and/or geometric shape of the second opening 132 can be adjusted to fit a specific drug delivery application, the opening 132 is substantially rectangular in shape.

In accordance with yet another illustrative aspect, the bent path 128 comprises a substantially semi-circular portion that is connected to the conduit for receiving the formulation from the fluid delivery device 104 and the channel 127. In accordance with this illustrative aspect, the bent path 128 terminates at the second opening 132, which in turn, is positioned substantially orthogonally relative to the substantially semi-circular portion of the bent path 128.

Once the formulation completely travels and circumnavigates the channel 127 and reaches the distal end 112a of the one or more outlets 112, it is now ready to be dispensed onto the surface or coat of the animal. As explained above, to spread the formulation evenly over a surface area of the animal, the outlet 112 can penetrate the animal's fur and thereby reach the animal's skin. To accomplish this, the outlet 112 may include one or more prongs 129 for assisting with the dispensing of the formulation onto the surface of the animal. In accordance with certain embodiments, the prongs 129 comprise spaced feet or tines that are configured to penetrate the fur of the animal 102 so that the applicator 106 can substantially reach or touch the surface of the animal's body during the dispensing of the formulation. This penetration allows a more efficient topical and transdermal release of the agent. In addition, those of skill in the drug delivery and fluid dispensing arts will understand and appreciate that the addition of prongs or other such structural projections from the outlet 112 will discourage capillary action or attraction (i.e., will stop the formulation from moving upwardly along the outside of the outlet) from happening during the dispensing action. The minimization and/or elimination of such capillary action effects are particularly beneficial when dealing with formulations that can be considered harmful and/or dangerous.

The present invention also includes a single dose transdermal formulation comprising a therapeutically effective amount of a composition comprising fentanyl, a penetration enhancer selected from the group consisting of long chain alkyl para-aminobenzoate, long chain alkyl dimethyl-para-aminobenzoate, long chain alkyl cinnamate, long chain alkyl methoxycinnamate, long chain alkyl salicylate, octyl dimethyl-para-aminobenzoate, octyl para-methoxycinnamate, octyl salicylate, or mixtures thereof, and a volatile liquid selected from the group consisting of ethanol, ethyl acetate, isopropanol, acetone, ethyl formate, methanol, methyl acetate, methyl ethyl ketone, pentan, chloroform, or mixtures thereof suitable for administration. In one embodiment, the penetration enhancer is octyl salicylate. In one embodiment, the volatile liquid is isopropanol. In some embodiments, the composition comprises fentanyl at a dose of about 2.7 mg per kg of canine body weight. In some embodiments, the single dose transdermal formulation controls pain in the canine for an effective period of time. In some embodiments, an effective period of time comprises a period of at least 24 hours, a period of at least 48 hours, a period of at least 72 hours, a period of at least 96 hours, or a period of at least 7 days. In one embodiment, the single dose transdermal formulation is administered once every at least 48 hours. In another embodiment, the single dose transdermal formulation is administered once every at least 72 hours. In yet another embodiment, the single dose transdermal formulation is administered once every at least 96 hours. In yet another embodiment, the single dose transdermal formulation is administered once every at least 7 days.

According to the methods of the present invention, the term "single dose transdermal formulation" includes embodiments wherein the composition can be transdermally administered as a single application and as multiple applications. In one embodiment, a single dose transdermal formulation of the composition can be transdermally administered to a canine in a single application at one location on the canine's skin. In another embodiment, a single dose transdermal formulation of the composition can be transdermally administered to a canine in multiple applications at more than one location on the canine's skin. In one embodiment, a single dose transdermal formulation of the composition is transdermally administered to a canine in a single application at one location on the canine's skin, wherein the single application is up to about 0.5 mL of a solution of the composition. In one embodiment, a single dose transdermal formulation of the composition can be transdermally administered to a canine in multiple applications at a single location on the canine's skin. In another embodiment, a single dose transdermal formulation of the composition is transdermally administered to a canine in multiple applications at a single location on the canine's skin, wherein each application has up to about 0.5 mL of a solution of the composition. In another embodiment, a single dose transdermal formulation of the composition is transdermally administered to a canine in multiple applications at more than one location on the canine's skin, wherein each application is up to about 0.5 mL of a solution of the composition. In embodiments wherein multiple applications of the composition are utilized, the multiple applications can be administered to the canine over a reasonable duration of time.

The following embodiments are also contemplated:

1. A method of controlling pain comprising transdermally administering to a canine in need thereof a therapeutically effective amount of a composition comprising fentanyl, a penetration enhancer, and a volatile liquid, wherein the composition is a solution.
2. The method of clause 1 wherein the transdermal administration is applied to a dorsal location of the canine.
3. The method of clause 1 wherein the transdermal administration is applied to a ventral location of the canine.
4. A method of controlling pain comprising transdermally administering to a canine in need thereof a therapeutically effective amount of a composition comprising fentanyl, a penetration enhancer, and a volatile liquid, wherein the composition is in a solution, and wherein the transdermal administration is applied to a dorsal location of the canine.
5. The method of any one of clauses 1 to 4 wherein the composition is administered as a single dose.
6. The method of any one of clauses 1 to 5 wherein the pain is controlled for an effective period of time.
7. The method of clause 6 wherein the effective period of time is about 96 hours.
8. A method of treating pain comprising transdermally administering to a canine in need of treatment a therapeutically effective amount of a composition comprising fentanyl, a penetration enhancer, and a volatile liquid, wherein the composition is administered as a single dose, and wherein the single dose is effective for the treatment of pain for about 96 hours.
9. The method of clause 8 wherein the transdermal administration is applied to a dorsal location of the canine.
10. The method of clause 8 wherein the transdermal administration is applied to a ventral location of the canine.
11. The method of any one of clauses 1 to 10 wherein the penetration enhancer is octyl salicylate.
12. The method of any one of clauses 1 to 11 wherein the volatile liquid is isopropanol.
13. The method of any one of clauses 1 to 12 wherein the pain is associated with a surgery performed or to be performed on the canine.
14. The method of clause 13 wherein the surgery is an orthopedic surgery.
15. The method of clause 13 wherein the surgery is a soft tissue surgery.
16. The method of any one of clauses 13 to 15 wherein the composition is administered to the canine about 2 to about 4 hours prior to the surgery.
17. The method of clause 16 wherein the composition is administered as a single dose.
18. The method of any one of clauses 1 to 17 wherein the composition is administered as a single unit dose.
19. The method of any one of clauses 1 to 18 wherein the composition comprises about 0.1 to about 10% (w/v) of fentanyl, about 0.1 to about 10% (w/v) of the penetration enhancer, and about 80 to about 99.8% (w/v) of the volatile liquid.
20. The method of any one of clauses 1 to 19 wherein the composition comprises about 3 to about 7% (w/v) of fentanyl, about 3 to about 7% (w/v) of the penetration enhancer, and about 86 to about 94% (w/v) of the volatile liquid.
21. The method of any one of clauses 1 to 20 wherein the composition comprises about 5% (w/v) of fentanyl, about 5% (w/v) of the penetration enhancer, and about 90% (w/v) of the volatile liquid.
22. The method of clause 21 wherein the penetration enhancer is octyl salicylate and the volatile liquid is isopropanol.
23. The method of any one of clauses 1 to 22 wherein the fentanyl is at a dose of about 0.1 to about 10 mg/kg of weight of the canine.
24. The method of any one of clauses 1 to 23 wherein the fentanyl is at a dose of about 1 to about 5 mg/kg of weight of the canine.
25. The method of any one of clauses 1 to 24 wherein the fentanyl is at a dose of about 2.7 mg/kg of weight of the canine.
26. The method of any one of clauses 1 to 25 wherein the composition is administered with one or more other therapeutic ingredients.
27. The method of any one of clauses 1 to 26 wherein the composition is administered using a transdermal dispensing apparatus.
28. A single dose transdermal formulation comprising a therapeutically effective amount of a composition in solution, wherein the composition comprises fentanyl, a penetration enhancer selected from the group consisting of long chain alkyl para-aminobenzoate, long chain alkyl dimethyl-para-aminobenzoate, long chain alkyl cinnamate, long chain alkyl methoxycinnamate, long chain alkyl salicylate, octyl dimethyl-para-aminobenzoate, octyl para-methoxycinnamate, octyl salicylate, or mixtures thereof, and a volatile liquid selected from the group consisting of ethanol, ethyl acetate, isopropanol, acetone, ethyl formate, methanol, methyl acetate, methyl ethyl ketone, pentan, chloroform, or mixtures thereof.

29. The formulation of clause 28 suitable for administration at a dose of about 0.1 to about 10 mg of fentanyl per kg of canine body weight.

30. The formulation of any one of clauses 28 or 29 suitable for administration at a dose of about 1 to about 5 mg of fentanyl per kg of canine body weight.

31. The formulation of any one of clauses 28 to 30 suitable for administration at a dose of about 2.7 mg of fentanyl per kg of canine body weight.

32. The formulation of any one of clauses 28 to 31 which is administered once every at least 72 hours.

33. The formulation of any one of clauses 28 to 31 which is administered once every at least 96 hours.

In each of the following examples, the composition of the present invention is administered to canines as a solution formulation. The embodiment of the composition of the present invention utilized in each example comprised fentanyl at a concentration of 5% weight/volume (50 mg/mL), octyl salicylate at a concentration of 5% weight/volume (50 mg/mL), and isopropanol.

EXAMPLE 1

Pharmacokinetics of a Fentanyl Composition Administered as a Single Transdermal Dose at a Ventral Location of Canines The pharmacokinetics of the composition of the present invention (comprising fentanyl, a penetration enhancer, and a volatile liquid, wherein the composition is a solution) can be examined following a single transdermal administration at a ventral location of canines. Eighteen adult beagle canines can be divided into three groups of six canines (three males and 3 females). Each group can be administered a single dose of the composition of the present invention comprising a fentanyl concentration of 1.3 (25), 2.6 (50) or 5.2 mg/kg (100 µL/kg). The dose can be transdermally applied as a single dose to clipped, ventral abdominal skin from approximately the umbilicus caudally using a 1-mL tuberculin syringe. Immediately following dosing, collars can be placed on each canine through 72 hours to prevent direct licking of the application site. Serial jugular venous blood samples can be collected at 0 (pre-dosing), 1, 2, 4, 6; 8, 12, 24, 36, 48, 60, 72, 84, 96, 108, 120, 144, 168, 240, 336, 408 and 504 hours after dosing and assayed for fentanyl by LC/MS/MS.

Following administration of a single transdermal dose, fentanyl is absorbed from the ventral abdominal application site within hours of application through 21 days in a dose-dependent manner (see Table 2). Fentanyl is rapidly detected with a mean absorption lag time ($t_{lag}$) of 0.333 hours in the 1.3 mg/kg group and 0 in the other two treatment groups. The mean maximum observed plasma concentration ($C_{max}$) increased with increasing doses of fentanyl and were calculated at 2.28, 2.67 and 4.71 ng/mL in the 1.3, 2.6 and 5.2 mg/kg dose groups, respectively. The mean time that $C_{max}$ was achieved ($t_{max}$) in all groups ranged from approximately 50 to 60 hours.

TABLE 2

Plasma fentanyl concentrations following application of 1.3, 2.6 or 5.2 mg/kg of the composition of the present invention as a single dose to the ventral abdomen to canines

| | Fentanyl Dose mg/kg (µL/kg) | | | | | |
|---|---|---|---|---|---|---|
| | 1.3 (25) | | 2.6 (50) | | 5.2 (100) | |
| Time (hr) | Mean (ng/mL) | SD | Mean (ng/mL) | SD | Mean (ng/mL) | SD |
| 0 | 0.000 | 0.000 | 0.000 | 0.000 | 0.000 | 0.000 |
| 1 | 0.037 | 0.031 | 0.083 | 0.028 | 0.167 | 0.107 |
| 2 | 0.108 | 0.062 | 0.221 | 0.058 | 0.513 | 0.220 |
| 4 | 0.199 | 0.100 | 0.364 | 0.077 | 0.876 | 0.509 |
| 6 | 0.359 | 0.271 | 0.592 | 0.127 | 1.173 | 0.536 |
| 8 | 0.492 | 0.305 | 0.864 | 0.201 | 1.875 | 0.802 |
| 12 | 0.699 | 0.376 | 1.192 | 0.321 | 2.851 | 1.214 |
| 24 | 0.796 | 0.346 | 1.383 | 0.272 | 3.387 | 1.141 |
| 36 | 1.598 | 0.549 | 2.069 | 0.631 | 3.692 | 0.828 |
| 48 | 1.733 | 0.877 | 2.244 | 1.361 | 3.230 | 0.690 |
| 60 | 1.864 | 1.016 | 2.013 | 1.093 | 3.608 | 1.019 |
| 72 | 1.314 | 0.582 | 1.613 | 0.653 | 3.246 | 0.773 |
| 84 | 0.724 | 0.456 | 1.194 | 0.592 | 3.985 | 2.078 |
| 96 | 0.761 | 0.364 | 1.131 | 0.455 | 3.288 | 1.091 |
| 108 | 0.744 | 0.759 | 1.336 | 0.727 | 2.886 | 0.749 |
| 120 | 0.565 | 0.233 | 1.268 | 0.264 | 2.594 | 0.708 |
| 144 | 0.286 | 0.162 | 0.663 | 0.376 | 1.592 | 0.162 |
| 168 | 0.267 | 0.115 | 0.615 | 0.343 | 1.597 | 0.415 |
| 240 | 0.085 | 0.045 | 0.274 | 0.208 | 0.914 | 0.426 |
| 336 | 0.020 | 0.033 | 0.085 | 0.064 | 0.377 | 0.229 |
| 408 | 0.006 | 0.015 | 0.070 | 0.069 | 0.198 | 0.138 |
| 504 | 0.005 | 0.012 | 0.020 | 0.023 | 0.185 | 0.140 |

Mean elimination half-lives were 53.7, 69.6 and 103 hours in the 1.3, 2.6 and 5.2 mg/kg dose groups, respectively. These observations are in marked contrast to the fentanyl half-life following an intravenous injection of fentanyl citrate, where the half-life ranges from 0.76 to 6.0 hours.

Plasma fentanyl concentrations less than the lower limit of quantification (LLOQ, 0.025 ng/mL) were set equal to zero ng/mL for descriptive statistic calculations. The mean area under the plasma concentration-time curve calculation from time 0 to the time of the last sample at or above the lower limit of quantification LLOQ ($AUC_{0-LLOQ}$) from lowest to highest dose groups were 157, 269 and 645 ng·hour/mL, and were dose proportional where $R^2$ was 0.9818.

A presumed minimum effective plasma concentration (MEC) of 0.2 to 1.2 ng/mL was used in the present example. Mean plasma fentanyl concentrations for the 1.3 mg/kg dose group remained at or above the lower and higher end of the MEC range from 4 to 168 hours and 36 to 72 hours, respectively. In contrast, at the 2.6 mg/kg dose, the mean plasma fentanyl concentrations remained ≥0.2 ng/mL from 2 to 240 hours and ≥1.2 ng/mL from 12 to approximately 84-120 hours. With the higher dose of 5.2 mg/kg, mean concentrations remained 0.2 ng/mL from 1 to 504 hours and ≥1.2 ng/mL from 6 to 168 hours. Therefore, the onset of a 1.3 mg/kg dose in a canine could be from 4 to 36 hours with a duration of 3 to 7 days. For a dose of 2.6 mg/kg, the onset could be from 2 to 12 hours with a duration of 3.5 to 10 days. Finally, for a dose of 5.2 mg/kg, the onset could be from 1 to 8 hours with a duration of 7 to 17 days.

To establish a dose, both safety and effectiveness must be considered. In human beings, a dose limiting effect is opioid-induced hypercapnia and respiratory depression. Such a profound response in humans has resulted in contraindication of a fentanyl patch for post-operative pain. In contrast, this is not a problem in canines in that spontaneous respirations are maintained independent of fentanyl concentration. Plasma fentanyl concentrations as high as approximately 80 ng/mL are not fatal and reduce the respiratory rate by only approximately 11 breaths/minute (50%) in spontaneously breathing canines. Additionally, the respiratory rate, oxygen consumption and blood gases ($pCO_2$, $pO_2$, and pH) do not change further as concentrations increase above 100 ng/ml.

The mean $C_{max}$ from the lowest to the highest dose in the present study were 2.28, 2.67 and 4.71 ng/mL and is well below concentrations that have a clinical impact on respiratory rates in canines. The primary dose limiting effect appeared to be decreased appetite and sedation in the 5.2 mg/kg dose group. One canine in this dose group required parenteral fluid therapy and forced feeding from 72 to 96 hours due to lack of food and water intake and 4 canines were sedated for 3 days. The 2.6 mg/kg group did not have any adverse events and had a faster presumed onset of action and longer duration than the 1.3 mg/kg group.

In summary, the 2.6 mg/kg (50 µL/kg) fentanyl dose group demonstrated a more rapid onset of action and longer duration of action compared to the 1.3 mg/kg fentanyl dose group following administration to a ventral location of canines. Furthermore, the 2.6 mg/kg fentanyl dose group demonstrated fewer observed adverse events compared to the 5.2 mg/kg fentanyl dose group.

EXAMPLE 2

Pharmacokinetics of a Fentanyl Composition Administered as a Single Transdermal Dose at a Ventral Location Compared to a Dorsal Location of Canines The pharmacokinetics of the composition of the present invention can be examined following a single transdermal administration of the composition to different anatomical sites on a canine. Generally, application of transdermal drugs to different anatomical sites can result in different absorption characteristics. There may be advantages of applying the composition of the present invention to sites other than the ventral abdomen. For example, dorsal inter-scapular application allows ambulatory canines to be walked to and from a treatment area for ease of application and is far from a laparotomy surgical site. However, different transdermal application sites are known to result in dissimilar drug delivery characteristics. The abdomen versus back skin in canines has been shown to differ with regard to blood flow and therefore different absorption characteristics may be apparent when drugs are applied to these sites. Therefore, the pharmacokinetics of the composition of the present invention may differ when the composition is applied topically to the ventral abdominal versus the dorsal inter-scapular areas of canines.

Forty purpose-bred laboratory beagle canines (Marshall BioResources, North Rose, N.Y.) were selected for the present study (20 males and 20 females, all 6 to 8 months of age at the time of dosing). Canines were administered 2.6 mg/kg (50 µL/kg) of the composition of the present invention applied as a single dose to the dorsal interscalpular region or ventral abdominal skin near the umbilicus. Canines were randomly allotted to dorsal or ventral dosing in parallel study design.

The mean plasma fentanyl concentrations by application site are displayed in Table 3. Plasma fentanyl concentrations rose more rapidly following dorsal application and persisted longer in the ventral application group. Mean plasma fentanyl concentrations remained above 0.6 ng/mL from 4-96 hours in the dorsal application group and 8-144 hours in the ventral application group.

TABLE 3

Plasma fentanyl concentrations by treatment group (n = 20/group) following administration of the composition of the present invention

| | Ventral Application | | | Dorsal Application | | |
|---|---|---|---|---|---|---|
| Time (hour) | Mean (ng/mL) | Standard Deviation (ng/mL) | C.V. (%) | Mean (ng/mL) | Standard Deviation (ng/mL) | C.V. (%) |
| 0 | 0.000 | 0.000 | NA | 0.000 | 0.000 | NA |
| 2 | 0.189 | 0.298 | 158.1% | 0.319 | 0.265 | 83.1% |
| 4 | 0.425 | 0.384 | 90.3% | 0.920 | 1.028 | 111.7% |
| 8 | 0.796 | 0.294 | 36.9% | 1.18 | 0.215 | 18.3% |
| 12 | 1.28 | 0.557 | 43.5% | 1.65 | 0.391 | 23.7% |
| 24 | 1.79 | 0.775 | 43.3% | 1.50 | 0.401 | 26.8% |
| 36 | 1.48 | 0.728 | 49.1% | 1.36 | 0.453 | 33.3% |
| 48 | 1.59 | 1.18 | 73.9% | 1.35 | 0.483 | 35.8% |
| 72 | 1.14 | 0.571 | 50.2% | 0.725 | 0.200 | 27.6% |
| 96 | 0.907 | 0.332 | 36.6% | 0.61 | 0.20 | 33.1% |
| 120 | 0.755 | 0.204 | 27.1% | 0.458 | 0.157 | 34.4% |
| 144 | 0.835 | 0.714 | 85.5% | 0.461 | 0.0887 | 19.2% |
| 168 | 0.536 | 0.123 | 22.9% | 0.315 | 0.0790 | 25.1% |
| 216 | 0.411 | 0.117 | 28.5% | 0.278 | 0.0927 | 33.4% |
| 264 | 0.343 | 0.169 | 49.3% | 0.178 | 0.0848 | 47.6% |
| 336 | 0.206 | 0.142 | 68.7% | 0.0842 | 0.0770 | 91.4% |
| 408 | 0.129 | 0.133 | 102.6% | 0.0418 | 0.0646 | 154.5% |
| 504 | 0.074 | 0.090 | 120.6% | 0.000 | 0.000 | NA |

NA: Not applicable

The pharmacokinetic parameters by application site group are summarized in Table 4. The $C_{max}$ was 2.34±1.29 (mean±standard deviation) and 2.02±0.84 ng/mL for the ventral and dorsal application groups, respectively. The $t_{max}$ was 40.2±29.5 and 24.8±17.8 hours in the ventral and dorsal application site groups, respectively. The terminal elimination half-lives ($t_{1/2}$) for both groups were similar with values of 137±58.9 and 117±56.6 hours for the ventral and dorsal application site groups, respectively. Less than 20% of the $AUC_{0-\infty}$ was extrapolated for both groups, indicating that $AUC_{0-LLOQ}$ sufficiently reflects the extent of exposure.

TABLE 4

Pharmacokinetic parameters by treatment group (n = 20/group) following administration of the composition of the present invention.

| | Ventral Application | | Dorsal Application | |
|---|---|---|---|---|
| Parameter | Mean | Standard deviation | Mean | Standard deviation |
| $C_{max}$ (ng/mL) | 2.34 | 1.29 | 2.02 | 0.840 |
| $t_{max}$ (hour) | 40.2 | 29.5 | 24.8 | 17.8 |
| $AUC_{0-LLOQ}$ (ng · hour/mL) | 251 | 75.1 | 170 | 29.0 |
| $AUC_{0-\infty}$ (ng · hour/mL) | 282 | 82.5 | 198 | 33.9 |
| $AUC_{0-\infty}$ Extrapolated (%) | 11.6 | 5.06 | 13.4 | 7.40 |
| $t_{1/2}$ (hour) | 137 | 58.9 | 117 | 59.6 |

The bioequivalence analysis results are displayed in Table 5. The dorsal to ventral ratio of the geometric means for $AUC_{0-LLOQ}$ was 70.5% (90% CI [60.6-82.0%]) and for $C_{max}$ ratio of the geometric means was 93.1% (90% CI [73.4-118%]).

TABLE 5

Ratio (dorsal:ventral) of the geometric means and 90% confidence interval of selected pharmacokinetic parameters (n = 20/group).

| Parameter | Lower 90% Confidence Interval | Ration of the Geometric Means | Upper 90% Confidence Interval |
|---|---|---|---|
| $AUC_{0-LLOQ}$ | 60.6% | 70.5% | 82.0% |
| $C_{max}$ | 73.4% | 93.1% | 118% |

There were no adverse events in this study. A single canine in the dorsal application group had a plasma fentanyl concentration of 13.0 ng/mL at 96 hours compared to the group mean of 0.61 ng/mL. Moderate to severe sedation would be expected at concentrations near or above 15 ng/mL. No sedation or adverse events were noted at the time of the observed elevated concentration at 96 hours and the 72 and 120 hour plasma fentanyl concentrations in this subject were below 1.0 ng/mL. Therefore, the transient spike was considered spurious and was dropped from further pharmacokinetic analysis.

The absorption of the composition of the present invention in canines is not equivalent when applied to the dorsal interscapular area versus the ventral abdominal area. Absorption was more rapid for dorsally applied composition of the present invention, supporting a more rapid onset of action compared to ventral application. Whereas the mean time to achieve a concentration of 0.6 ng/mL was 4 hours for dorsal application, ventral application did reach this concentration until 8 hours following dosing. The more rapid absorption associated with dorsal application was also associated with a difference in mean duration above 0.6 ng/mL. The mean time to drop below 0.6 ng/mL for dorsal and ventral application was 96 and 144 hours, respectively (see Table 3).

Dorsal administration achieved an absorption rate of ≥2 µg/kg/hour from 2 to 144 hours following application with a peak of 9.8 µg/kg/hour occurring at 12 hours. In contrast, ventral administration achieved an absorption rate of ≥2 µg/kg/hour from 2 to 264 hours with a peak of 8.5 µg/kg/hour occurring at 24 hours. These results suggest that potentially analgesic infusion rates from the composition of the present invention are achieved within a few hours of application and are maintained for periods of up to 10 days.

In summary, both dorsal and ventral application sites resulted in absorption rates of greater than 2 µg/kg/hour within 2 hours of transdermal application to canines, but the dorsal site achieved mean plasma concentration of 0.6 ng/mL by 4 hours compared to 8 hours with ventral application. Therefore, dorsal application provides a more rapid onset of action. With such a rapid onset of action, the composition of the present invention could be applied to a canine as it enters the hospital as an anesthetic premedication with analgesic concentrations potentially occurring 2-4 hours prior to surgery. Without additional opioid administration, this single dose could have a duration of a minimum of 96 hours.

EXAMPLE 3

Pharmacokinetics of a Fentanyl Composition Administered as a Single Transdermal Dose at a Dorsal Location of Canines The pharmacokinetics of the composition of the present invention (comprising fentanyl, a penetration enhancer, and a volatile liquid, wherein the composition is a solution) can be examined following a single transdermal administration at a dorsal location of canines. Twenty purpose-bred laboratory beagle canines (10 males and 10 females) can be administered a single dose of the composition of the present invention (comprising 2.6 mg/kg of fentanyl) to the dorsal, interscapular region. Blood samples for plasma fentanyl analysis by LC-MS/MS can be collected from pre-dose administration through 21 days post-dose administration (i.e., collection at 0, 2, 4, 8, 12, 24, 36, 48, 72, 96, 120, 144, 168, 216, 264, 336, 408 and 504 hours after dosing). Pharmacokinetics can be determined using noncompartmental pharmacokinetic analysis methods.

Following administration of the composition of the present invention, the mean plasma fentanyl concentrations rose rapidly with all canines demonstrating measurable plasma fentanyl concentrations (>0.100 ng/mL) by 2 hours after dose administration (see Table 6). The mean plasma fentanyl concentrations reached the maximum value around 12 hours post-dose administration, and gradually declined thereafter until all samples were less than 0.100 ng/mL at 504 hours. The mean plasma fentanyl concentrations remained above 0.5 ng/mL from 4 through 96 hours post-dose administration.

TABLE 6

Mean concentration of fentanyl in canines (n = 20) following administration of the composition of the present invention.

| Time (hour) | Mean (ng/mL) | Standard Deviation (ng/mL) | C.V. (%) |
|---|---|---|---|
| 0 | 0.00 | 0.00 | NA |
| 2 | 0.319 | 0.265 | 83.1% |
| 4 | 0.920 | 1.03 | 112% |
| 8 | 1.18 | 0.215 | 18.2% |
| 12 | 1.65 | 0.391 | 23.7% |
| 24 | 1.50 | 0.401 | 26.7% |
| 36 | 1.36 | 0.453 | 33.3% |
| 48 | 1.35 | 0.483 | 35.8% |
| 72 | 0.725 | 0.200 | 27.6% |
| 96 | 1.23 | 2.78 | 226% |
| 120 | 0.458 | 0.157 | 34.3% |
| 144 | 0.461 | 0.0887 | 19.2% |
| 168 | 0.315 | 0.0790 | 25.1% |
| 216 | 0.278 | 0.0927 | 33.3% |
| 264 | 0.178 | 0.0848 | 47.6% |
| 336 | 0.0842 | 0.0770 | 91.4% |
| 408 | 0.0418 | 0.0646 | 155% |
| 504 | 0.00 | 0.00 | NA |

NA: Not applicable

The coefficient of variation (C.V.) of the plasma fentanyl samples was generally around 50%. A relatively high C.V. was observed at 96 hours due to single canine having a transiently high plasma fentanyl concentration of 13.0 ng/mL at 96 hours. The plasma fentanyl concentrations at the adjacent 72 and 120 hour samples for this subject were both below 1.0 ng/mL. No sedation or other side-effects were observed at 96 hours, even though sedation would be expected in a canine with a plasma fentanyl concentration of 13.0 ng/mL. The cause of the transient increase in the plasma fentanyl concentration is unknown.

The results from the noncompartmental pharmacokinetic analysis are displayed in Table 7. The mean $C_{max}$ was 2.58 ng/mL (2.59 standard deviation). However, the results were highly influenced by the single transiently high plasma fentanyl concentration of 13.0 ng/mL at 96 hours. Exclusion of this single sample from the mean and standard deviation calculation results in $C_{max}$ values of 2.02 and 0.840 ng/mL, respectively.

TABLE 7

Parameters from noncompartmental pharmacokinetic analysis (n = 20).

| Parameter | Mean | Standard deviation |
|---|---|---|
| $C_{max}$† (ng/mL) | 2.58 | 2.59 |
| $t_{max}$ (hour) | 29.0 | 23.6 |
| $AUC_{0\text{-}LLOQ}$ (ng · hour/mL) | 181 | 59.7 |
| $AUC_{0\text{-}\infty}$ (ng · hour/mL) | 206 | 64.4 |
| $AUC_{0\text{-}\infty}$ Extrapolated (%) | 11.8 | 7.48 |
| $t_{1/2}$ (hour) | 117 | 61.5 |

†Removal of single subject's 96 hour sample of 13.0 ng/mL results in a $C_{max}$ mean and standard deviation of 2.02 and 0.840 ng/mL, respectively.

The $t_{max}$ was 29.0 (23.6) hours and the $t_{1/2}$ was 117 (61.5) hours. The percent extrapolated $AUC_{0\text{-}\infty}$ was only 11.8 (7.48) %, indicating a sufficient portion of the plasma concentration-time profile was observed to accurately quantify the $AUC_{0\text{-}\infty}$ and $t_{1/2}$. The $AUC_{0\text{-}\infty}$ was 206 (64.4) ng·hour/mL, corresponding to a large bioavailability normalized clearance (i.e. Cl/F) of 13.5 (3.44) L/hr·kg. The exclusion of the single sample with a transiently high plasma concentration at 96 hours had minimal impact on the pharmacokinetic parameters other than $C_{max}$ and therefore results excluding this plasma sample are not presented for the other parameters.

Compared to the fentanyl transdermal patch use in canines at dose rates of 50 to 100 μg/h, the mean plasma fentanyl concentrations reached 0.6 ng/mL more rapidly following a 2.6 mg/kg dose of the composition of the present invention. Following administration of the composition, the mean plasma fentanyl concentrations reached 0.6 ng/mL within 4 hours of dose administration (see Table 6) compared to 10 to 30 hours with transdermal patch application. Thus, analgesic concentrations will be more rapidly reached following application of the composition of the present invention compared to transdermal fentanyl patches, reducing the time pre-surgery that the fentanyl must be administered. Additionally, the mean plasma fentanyl concentrations remained above 0.6 ng/mL for 92 hours following administration of the composition of the present invention, while they only remained above this concentration for 18 to 62 hours with the transdermal patch. The administration of 50 μg/h transdermal fentanyl patch in 6 male beagle canines resulted in relatively constant plasma fentanyl concentrations from 24 to 72 hours post-application with a mean concentration of approximately 1.6 ng/mL. In comparison, the mean plasma fentanyl concentration of the composition of the present invention gradually fell from 1.50 ng/mL at 24 hours to 0.725 ng/mL at 72 hours, with a mean concentration of 1.23 ng/mL (see Table 6).

The pharmacokinetic parameter results for the composition of the present invention (see Table 7) were similar to a recent study of the fentanyl transdermal patch where the mean $C_{max}$ and $t_{max}$ values were 2.1 ng/mL and 22 hours, respectively. In that study, the size of the patch applied depended on the canine bodyweight, with an approximate targeted dose of approximately 3 μg/hr/kg of bodyweight.

No adverse side-effects or application site skin reactions were observed during the study.

In summary, methods of the present invention administered at a dorsal location of canines can overcome the main limitations of orally or parenterally administered fentanyl and, in addition, many of the limitations of the fentanyl transdermal patch.

EXAMPLE 4

Population Pharmacokinetics of a Fentanyl Composition Administered as a Single Transdermal Dose Administered to Canines Prior to Soft Tissue or Orthopedic Surgery A study of the methods of the present invention can be undertaken to determine transdermal administration of the composition of the present invention in canines undergoing surgical procedures. Enrolled canines can be randomized to receive either the composition of the present invention or the positive control subcutaneous oxymorphone (Opana® Injection, Endo Pharmaceuticals Inc., Chadds Ford, Pennsylvania). Canines randomized to receive the composition of the present invention treatment group can be administered a single 2.7 mg/kg (54 μL/kg) fentanyl dose to the dorsal scapular area two to four hours prior to either orthopedic or soft-tissue surgery. Canines randomized to the positive control treatment group can be administered oxymorphone subcutaneously 2-4 hours prior to surgery, at the time of extubation, and every 6 hours through 90 hours post-extubation. Oxymorphone HCl can be administered at the FDA approved dose in canines of approximately 0.1-0.2 mg/kg.

Plasma fentanyl concentrations can be determined from 215 canines following administration of a single dose of the composition of the present invention. A population pharmacokinetic model was fit to the resulting data, with a 1-compartment open pharmacokinetic model with first-order absorption and an absorption lag-time best fitting the data. No tested clinical covariates had a significant effect on the pharmacokinetics of the composition of the present invention. The final model adequately described the population pharmacokinetics and gave results consistent with laboratory pharmacokinetic studies in healthy canines.

Using the final model population median parameter estimates (see Table 8), the estimated area under the fentanyl plasma concentration-time curve from time 0 to infinity ($AUC_{0\text{-}\infty}$) was 220 ng·hr/mL for a "typical" subject. Additionally, the estimated average concentration from 0 to 4 days (96 hours) for a typical clinical patient was 1.32 ng/mL, which is likely to be analgesic in canines. The estimated maximum plasma concentration ($C_{max}$) and time of $C_{max}$ occurrence ($t_{max}$) was 1.83 ng/mL and 13.6 hours for a typical subject, respectively. Finally, the estimated terminal half-life ($t_{1/2}$) was 74.0 hr for a typical subject. The long $t_{1/2}$ is consistent with the previously recognized flip-flop pharmacokinetics of the composition of the present invention since intravenously administered fentanyl has a $t_{1/2}$ of approximately 0.76 to 6.0 hours.

TABLE 8

Population pharmacokinetic model parameter estimates (n = 215 subjects). Values represented as the estimate (standard error).

| Parameter | Median | Variance ($\omega^2$) |
|---|---|---|
| $t_{lag}$ (hr) | 0.552 (1.63) | 0.0517 (12.3) |
| $k_a$ (1/hr) | 0.267 (0.167) | 0.0581 (0.745) |
| V/F ($10^3$ L/kg) | 1.26 (0.130) | 0.346 (0.0694) |
| $k_e$ (1/hr) | 0.00937 (0.00165) | 0.00204 (0.140) |
| b* | 0.301 (0.0765) | NA |

*Scaler of the proportional residual error model;
NA: Not applicable

The plasma fentanyl concentrations were sustained over days in the range considered to be analgesic for postoperative pain in canines. The time to reach 0.5 ng/mL in a typical canine patient administered the composition of the present invention was 1.60 hours, compared to 10 to 30 hours with fentanyl transdermal patch application in canines. The administration of 50 µg/h fentanyl transdermal patch in 6 male beagle canines resulted in mean plasma fentanyl concentrations of approximately 1.6 ng/mL from 24 to 72 hours post-application. In comparison, the observed mean concentration of plasma fentanyl with the composition in the present study was 1.82 ng/mL from 24 to 72 hours post-application.

In summary, following dorsal administration to canines, a 1-compartment open pharmacokinetic model with first order absorption and an absorption lag-time best described the pharmacokinetics of a single application of the composition of the present invention at a dose of 2.7 mg/kg of fentanyl in the target clinical population. For canines administered the composition of the present invention, both the observed and predicted plasma fentanyl concentrations were sustained over days in the range considered to be analgesic for postoperative pain in canines.

EXAMPLE 5

Comparison of a Transdermal Fentanyl Composition and Oxymorphone for the Control of Post-Operative Pain in Canines The safety and effectiveness of the composition of the present invention compared to oxymorphone hydrochloride can be examined for the control of post-operative pain over a period of four days. Canines can be randomly assigned to a single transdermal dose of the composition of the present invention (2.7 mg/kg [1.2 mg/lb]) applied 2-4 hours prior to surgery or oxymorphone hydrochloride (0.1-0.2 mg/kg [0.22-0.44 mg/lb]) administered subcutaneously 2-4 hours prior to surgery and then administered every 6 hours subsequently through 90 hours post-surgery. Canines randomized to receive the composition of the present invention can be administered a single dose of 2.7 mg/kg (1.2 mg/lb [approximately 50 µL/kg]) to the dorsal scapular area 2-4 hours prior to surgery. Pain can be evaluated by blinded observers using the Glasgow modified pain scale and the a priori criteria for treatment failure was a pain score≥8 (20 maximum score) or adverse events necessitating withdrawal.

In the present example, 502 canines of various breeds were enrolled and were approximately equally divided between the composition of the present invention (N=249) and oxymorphone (N=253). Canines were divided between soft tissue (N=250) and orthopedic surgical procedures (N=251). Four canines treated with the composition of the present invention were withdrawn due to lack of pain control (pain score≥8) and 1 due to death unrelated to fentanyl. Eight oxymorphone-treated canines were withdrawn due to lack of pain control, 18 due to severe adverse events and 1 due to death unrelated to oxymorphone.

The primary variable for determining effectiveness was a non-inferiority evaluation of the treatment failure rate of the composition of the present invention (i.e., a composition comprising fentanyl) and oxymorphone. The upper bound for the margin of difference between fentanyl-oxymorphone treatment failure rates was to be no greater than 15% for fentanyl to be considered non-inferior to oxymorphone. The dropout rate for fentanyl was 2.01% and the dropout rate for oxymorphone was 10.76% with a mean difference of −8.7% (see Table 9). The one-sided upper 95% confidence bound was −6.2%, which was not greater than the a priori selected margin difference of 15%. Therefore, based on treatment failure rate, administration of the composition of the present invention (i.e., a composition comprising fentanyl) was non-inferior to oxymorphone.

TABLE 9

Non-inferiority analysis of treatment failures.

| Transdermal Fentanyl Solution (N = 249) Treatment Failures | | Oxymorphone (N = 251) Treatment Failures | | Difference | | |
|---|---|---|---|---|---|---|
| n | % | n | % | Mean | SE | Upper 95% CI* |
| 4 | 2.01 | 27 | 10.76 | −8.7 | 1.5 | −6.2 |

*The transdermal fentanyl solution dropout rate was non-inferior to the oxymorphone dropout rate as the upper 95% CI of the percent difference was contained within the 15% a priori margin of difference.

A secondary non-inferiority analysis compared fentanyl to oxymorphone with respect to the pain intensity scores at each pain assessment period. Pain scores were highest 2 hours following extubation in both groups where mean values were 2.32 in fentanyl- and 2.64 in oxymorphone-treated canines. Pain scores declined over the 4 day study duration such that by Day 4, mean pain scores ranged from 0.830 in fentanyl- and 1.28 in oxymorphone-treated canines. At all time points with the exception of the 1 hour pain assessment, the composition of the present invention was non-inferior to oxymorphone.

An additional secondary non-inferiority analysis compared fentanyl to oxymorphone with respect to SPID (see Table 10). The mean sum of pain intensity scores was 18.636 for fentanyl- and 21.662 for oxymorphone-treated canines, respectively. The upper bound for the SPID between fentanyl-oxymorphone was to be no greater than 26% for fentanyl to be considered non-inferior to oxymorphone. The upper bound for the SPID between fentanyl-oxymorphone was 0.432, which was not greater than 26%. Therefore, based on SPID, the composition of the present invention was non-inferior to oxymorphone.

TABLE 10

Sum of pain intensity score summary statistics over the entire post-surgical period, SPID and the one-sided upper 95% confidence bound for the difference.

| Statistic | Transdermal Fentanyl Solution | Oxymorphone | SPID | One-Sided Upper 95% CI* |
|---|---|---|---|---|
| Mean | 18.636 | 21.662 | −3.026 | 0.432 |
| N | 118 | 65 | | |
| SD | 12.563 | 15.333 | | |
| SE | 1.157 | 1.902 | | |
| Median | 15 | 19 | | |
| Min | 0 | 0 | | |
| Max | 55 | 72 | | |

*The SPID for fentanyl-oxymorphone was non-inferior as the upper 95% CI is contained within the 26% a priori margin of difference.

Canines with sedation scores≥2 prior to a scheduled pain assessment were not scored for pain because excess sedation interfered with the pain assessor's ability to adequately evaluate analgesia by use of the modified Glasgow composite pain scale. At no time was the mean sedation score≥2 in either treatment group. Sedation scores were highest at the first pain assessment time, 1 hour post-extubation where the mean sedation scores were 1.67 and 1.98 in the fentanyl- and oxymorphone-treated canines, respectively. By 6 hours post-extubation, mean sedation scores in both groups were less than 1 (mild); 0.81 and 0.97 for fentanyl and oxymorphone, respectively. At 1 hour postextubation, 49% of fentanyl-treated canines had a sedation scores≥2 and by 12 hours this had diminished to 7% of canines. By 24 hours, 3% of fentanyl-treated canines had a sedation scores≥2 and none beyond 48 hours. The number of oxymorphone treated canines with sedation scores≥2 was greater at each assessment period compared to fentanyl. At 1 hour post-extubation, 70% of oxymorphone-treated canines had a sedation scores≥2 and 11% of canines remained moderated sedated at 12 hours. By 24 hours, 7% of oxymorphone-treated canines had a sedation scores≥2 and 3% to 0.9% of canines were moderately sedated throughout remaining 4 day study period.

Overall, adverse events associated with oxymorphone were greater in both number and severity compared to the composition of the present invention. There were a total of 56 individual adverse events reported in 44 (17.7%) fentanyl-treated canines; 46 were categorized as mild, 9 moderate and 1 severe (see Table 11). In oxymorphone-treated canines, there were a total of 228 adverse events reported in 84 (33.7%) canines; 125 were categorized as mild, 75 moderate and 28 severe. The incidence of adverse events in fentanyl-treated canines was infrequent over time with a slightly greater incidence for some adverse events within the first 48 hours of surgery (see Table 12). Over the first 48 hours, the most frequent adverse events were diarrhea ranging from 0.4-2%, emesis ranging from 0-1.6%, hypothermia ranging from 1.5-4.4% and anorexia ranging from 0-0.8%. The incidence of adverse in oxymorphone-treated canines was higher in some categories compared to fentanyl and persisted throughout the 4 day study period (see Table 13). Over the 4 day study period, emesis ranged from 1.6-8.7% and hypothermia ranged from 1.4-9.5%. There were two deaths in this study; one each in the fentanyl- and oxymorphone-treated groups. In both instances, the deaths were judged to be unrelated to investigational or control drug treatment.

TABLE 11

The number of adverse events in each treatment group by adverse event severity category.

| Adverse Event Severity Category | Number of Adverse Events | |
| --- | --- | --- |
| | Transdermal Fentanyl Solution (N = 249) | Oxymorphone (N = 253) |
| Mild | 46 | 125 |
| Moderate | 9 | 75 |
| Severe | 1 | 28 |
| Total | 56 | 228 |

TABLE 12

Adverse events by study day in dogs treated with transdermal fentanyl solution.

| Adverse Event (N = 249) | Day 0 N (%) | Day 1 N (%) | Day 2 N (%) | Day 3 N (%) | Day 4 N (%) |
| --- | --- | --- | --- | --- | --- |
| Diarrhea | 1 (0.4%) | 5 (2.0%) | 2 (0.8%) | 1 (0.4%) | 0 (0.0%) |
| Emesis | 0 (0.0%) | 4 (1.6%) | 2 (0.8%) | 2 (0.8%) | 0 (0.0%) |
| Hypothermia | 4 (1.6%) | 11 (4.4%) | 0 (0.0%) | 0 (0.0%) | 0 (0.0%) |
| Pyrexia | 0 (0.0%) | 0 (0.0%) | 1 (0.4%) | 1 (0.4%) | 0 (0.0%) |
| Anorexia | 0 (0.0%) | 2 (0.8%) | 1 (0.4%) | 0 (0.0%) | 0 (0.0%) |

TABLE 12-continued

Adverse events by study day in dogs treated with transdermal fentanyl solution.

| Adverse Event (N = 249) | Day 0 N (%) | Day 1 N (%) | Day 2 N (%) | Day 3 N (%) | Day 4 N (%) |
| --- | --- | --- | --- | --- | --- |
| Constipation | 0 (0.0%) | 0 (0.0%) | 0 (0.0%) | 0 (0.0%) | 0 (0.0%) |
| Hypersalivation | 0 (0.0%) | 0 (0.0%) | 0 (0.0%) | 0 (0.0%) | 0 (0.0%) |
| Conjunctivitis | 0 (0.0%) | 0 (0.0%) | 0 (0.0%) | 0 (0.0%) | 0 (0.0%) |
| Death | 0 (0.0%) | 0 (0.0%) | 0 (0.0%) | 1 (0.4%) | 0 (0.0%) |

TABLE 13

Adverse events by study day in dogs treated with oxymorphone.

| Adverse Event (N = 252) | Day 0 N (%) | Day 1 N (%) | Day 2 N (%) | Day 3 N (%) | Day 4 N (%) |
| --- | --- | --- | --- | --- | --- |
| Diarrhea | 3 (1.2%) | 3 (1.2%) | 5 (2.0%) | 4 (1.6%) | 0 (0.0%) |
| Emesis | 10 (4.0%) | 11 (4.4%) | 22 (8.7%) | 15 (6.0%) | 4 (1.6%) |
| Hypothermia | 16 (6.3%) | 24 (9.5%) | 4 (1.6%) | 5 (2.0%) | 4 (1.6%) |
| Pyrexia | 0 (0.0%) | 0 (0.0%) | 0 (0.0%) | 1 (0.4%) | 0 (0.0%) |
| Anorexia | 0 (0.0%) | 5 (2.0%) | 4 (1.6%) | 2 (0.8%) | 1 (0.4%) |
| Constipation | 0 (0.0%) | 1 (0.4%) | 0 (0.0%) | 0 (0.0%) | 0 (0.0%) |
| Hypersalivation | 5 (2.0%) | 1 (0.4%) | 1 (0.4%) | 0 (0.0%) | 1 (0.4%) |
| Conjunctivitis | 0 (0.0%) | 1 (0.4%) | 0 (0.0%) | 0 (0.0%) | 0 (0.0%) |
| Death | 0 (0.0%) | 0 (0.0%) | 1 (0.4%) | 0 (0.0%) | 0 (0.0%) |

In summary, a single dose of the composition of the present invention applied topically 2-4 hours prior to surgery is safe and effective for the control of pain associated with orthopedic and soft tissue surgery in canines and provides analgesia for at least 96 hours. A sustained, steady-state fentanyl delivery provided by a single preemptive dose of the composition of the present invention provides equianalgesia compared to repeated injections of oxymorphone over 96 hours with less adverse events.

EXAMPLE 6

Margin of Safety of a Single Transdermal Dose of a Fentanyl Composition Administered at Multiples of the Therapeutic Dose to Canines The margin of safety following application at a multiple dose of the composition of the present invention can be examined. Twenty-four healthy purpose bred laboratory mixed-breed hound canines (12 males/12 females) were administered a single placebo or increasing doses of the composition of the present invention to the ventral abdominal skin and observed for 14 days. Doses of the composition were administered at 2.6 (1×), 7.8 (3×), or 13.0 (5×) mg/kg based on canine body weight.

Plasma fentanyl concentrations increased with dose and were detectable (≥0.025 ng/mL) at the first sampling point 30 minutes post-dosing through 14 days in each group (see Table 14). Mean $C_{max}$ were 3.18, 7.27 and 13.5 ng/mL and AUC0-LLOQ were 323, 824 and 1272 ng·hour/mL in the 1×, 3× and 5× groups, respectively (see Table 15). Half-lives in all three dose groups were approximately 70 hours. Exposure to fentanyl, as measured by $AUC_{0-LLOQ}$, was dose proportional.

TABLE 14

Plasma fentanyl concentrations (ng/mL) summary statistics by treatment group (n = 6/group)

| Time (hr) | 1X (2.6 mg/kg) | | 3X (7.8 mg/kg) | | 5X (13.0 mg/kg) | |
|---|---|---|---|---|---|---|
| | Mean | SD | Mean | SD | Mean | SD |
| 0 | 0 | 0 | 0 | 0 | 0 | 0 |
| 0.5 | 0.02 | 0.02 | 0.18 | 0.19 | 0.17 | 0.03 |
| 1 | 0.20 | 0.11 | 0.57 | 0.36 | 1.04 | 0.36 |
| 2 | 0.51 | 0.24 | 1.66 | 0.79 | 2.30 | 0.46 |
| 4 | 1.00 | 0.36 | 3.34 | 1.53 | 4.48 | 1.26 |
| 8 | 1.87 | 0.33 | 4.38 | 1.94 | 8.38 | 3.48 |
| 12 | 3.00 | 0.95 | 6.03 | 2.34 | 12.20 | 5.01 |
| 24 | 2.82 | 0.92 | 6.30 | 0.79 | 12.68 | 3.54 |
| 36 | 2.11 | 0.82 | 4.72 | 1.34 | 11.18 | 3.81 |
| 48 | 1.80 | 0.44 | 5.05 | 1.63 | 8.51 | 3.22 |
| 60 | 2.35 | 0.79 | 5.04 | 1.40 | 9.19 | 1.81 |
| 72 | 2.03 | 0.93 | 4.45 | 2.09 | 7.19 | 2.21 |
| 96 | 1.47 | 0.31 | 3.83 | 2.22 | 5.54 | 2.70 |
| 120 | 0.97 | 0.29 | 3.47 | 2.04 | 3.75 | 1.74 |
| 144 | 1.01 | 0.42 | 2.63 | 1.88 | 3.29 | 2.13 |
| 168 | 0.60 | 0.22 | 1.66 | 0.62 | 1.85 | 0.65 |
| 192 | 0.35 | 0.18 | 1.11 | 0.37 | 1.19 | 0.40 |
| 216 | 0.36 | 0.22 | 1.06 | 0.44 | 1.29 | 0.57 |
| 240 | 0.27 | 0.18 | 1.05 | 0.33 | 1.00 | 0.47 |
| 264 | 0.30 | 0.23 | 0.87 | 0.33 | 1.04 | 0.44 |
| 288 | 0.23 | 0.14 | 0.71 | 0.19 | 0.96 | 0.45 |
| 312 | 0.10 | 0.06 | 0.34 | 0.13 | 0.40 | 0.22 |
| 336 | 0.15 | 0.10 | 0.53 | 0.16 | 0.58 | 0.19 |

SD: Standard deviation.

TABLE 15

Pharmacokinetic parameters by treatment group (n = 6/group).

| Parameter | 1X (2.6 mg/kg) | | 3X (7.8 mg/kg) | | 5X (13.0 mg/kg) | |
|---|---|---|---|---|---|---|
| | Mean | SD | Mean | SD | Mean | SD |
| $C_{max}$ (ng/mL) | 3.18 | 0.85 | 7.27 | 1.39 | 13.5 | 4.12 |
| $t_{max}$ (hour) | 16 | 6.20 | 28 | 21.0 | 28 | 22.3 |
| $AUC_{0-LLOQ}$ (ng · hour/mL) | 323 | 80.5 | 824 | 258 | 1272 | 315 |
| $AUC_{0-\infty}$ (ng · hour/mL) | 339 | 88.6 | 883 | 255 | 1333 | 326 |
| $AUC_{0-\infty}$ Extrapolated (%) | 4.74 | 3.10 | 7.13 | 3.14 | 4.63 | 2.03 |
| $t_{1/2}$ (hour) | 71.2 | 15.1 | 75.8 | 11.2 | 72.3 | 15.1 |

SD: Standard deviation

Sedation was not observed in the placebo group. A few incidences of slight sedation were observed in the 1× group over 24 hours beginning within 4 hours of dosing (see Table 16). In the 3× and 5× groups, sedation was evident within 1 hour of dosing through Day 5 and 4, respectively (see Table 16). Moderate to severe sedation was limited to the 3× and 5× groups, observed from 2.5 hours post-dose administration until Day 3. Canines in the 3× and 5× groups were supplemented with 40-60 mL/kg/day subcutaneous fluids (Normosol-R, Hospira, Inc., Lake Forest, Ill.) on Days 0 and 1 because it was determined that they were not consuming maintenance water quantities due to excess sedation.

TABLE 16

Mean sedation scores* by dose group (n = 6 per group) vs. time.

| Time | | | | | |
|---|---|---|---|---|---|
| Day | Hour | Control | 1X | 3X | 5X |
| 0 | 1 | 0 | 0 | 0.50 | 1.00 |
| 0 | 2.5 | 0 | 0 | 1.33 | 2.50 |
| 0 | 4 | 0 | 0.33 | 2.00 | 2.67 |
| 1 | 1 | 0 | 0.33 | 2.17 | 2.83 |
| 1 | 2.5 | 0 | 0.17 | 2.00 | 2.83 |
| 1 | 4 | 0 | 0.17 | 2.00 | 2.83 |
| 2 | 1 | 0 | 0 | 1.33 | 2.33 |
| 2 | 2.5 | 0 | 0 | 1.33 | 2.33 |
| 2 | 4 | 0 | 0 | 1.33 | 2.33 |
| 3 | — | 0 | 0 | 0.33 | 0.50 |
| 4 | — | 0 | 0 | 0.33 | 0.33 |
| 5 | — | 0 | 0 | 0.33 | 0 |
| 6 | — | 0 | 0 | 0 | 0 |
| 7 | — | 0 | 0 | 0 | 0 |
| 8 | — | 0 | 0 | 0 | 0 |
| 9 | — | 0 | 0 | 0 | 0 |
| 10 | — | 0 | 0 | 0 | 0 |
| 11 | — | 0 | 0 | 0 | 0 |
| 12 | — | 0 | 0 | 0 | 0 |
| 13 | — | 0 | 0 | 0 | 0 |
| 14 | — | 0 | 0 | 0 | 0 |

*0 = no sedation, 1 = slight, 2 = moderate, 3 = severe

Mean food consumption decreased in all treated dose groups following dosing. The greatest decrease in food consumption was in the 5× group where no food was consumed on Days 0 through 2. Food consumption had returned to pretreatment amounts by Day 4 in the 1× group and Day 6 in the 3× and 5× groups. Mean body weights decreased slightly in the 1× group over 7 days and to a slightly greater extent in the 3× and 5× groups. Over the 14 day study period there were 4, 1, 4 and 3 vomiting events in the placebo, 1×, 3× and 5× groups, respectively. Over the 14 day study period there were 1, 6, 21 and 25 abnormal feces occurrences, including dark or red stools and diarrhea or mucoid feces, in the placebo, 1×, 3× and 5× groups, respectively. Abnormal feces in the 1× group was limited to Days 1 to 3 whereas in the 3× and 5× groups, abnormal feces were more sporadic beginning at Day 4 through the end of the study. Salivation was seen in a one canine in the 1× group on Days 4 and 5, one canine in the 3× group on Days 2 and 3 and three canines in the 5× group on Days 2 to 3 with one observation on Day 10. Lacrimation was seen in one canine in the 3× group on Day 2. Miosis was observed in four canines in the 5× group on Days 0 and 1.

Mean heart rates decreased in a dose-dependent manner for 2 days following dose administration of the composition of the present invention and returned to rates similar to that in the placebo group from Day 3 through 14. The maximal decrease in heart rate was observed in the 5× dose group and was an approximately 50% decrease relative to the placebo controls. Mean respiration rates were more variable than heart rates, but they appeared to decrease slightly in a dose-dependent manner for 2 to 3 days after dose administration. However; unlike heart rate, the maximal decrease in the mean respiration rate was similar in both the 3× and 5× dose groups at approximately 30%. The mean rectal body temperatures decreased in a dose-dependent manner, and remained below the placebo control in all treated dose groups from 1 hour post-dose administration through Day 3 or 4. The maximum drop in body temperature was approximately 2, 3 and 4° C. on Day 1 in the 1×, 3× and 5× groups, respectively.

Diffuse, bilateral ocular lens opacities were reported on Day 3 in one 3× canine and three 5× canines by the attending veterinarian. A follow-up ophthalmic examination was conducted on Day 7 by the attending veterinarian and the ocular opacities were limited to one 3× group canine. A board-certified veterinary ophthalmologist was consulted to examine the canines on Day 8 and the Day 7 findings were confirmed by biomicroscopy following pharmacologic mydriasis. By Day 13, the lens opacities were not observed in the single 3× canine as confirmed by a veterinary ophthalmologist.

There were no arrhythmias or altered cardiac indices from the ECGs recorded on Days 3 and 13. All mean hematology and serum chemistry results remained within the normal range (see Tables 17, 18, and 19). The mean blood urea nitrogen (BUN) on Day 3 in both the 3× and 5× groups increased to 14.2 and 13.2 mg/dL, respectively but remained within the normal range. By Day 14, the BUN in both the 3× and 5× group were similar to Day −7 values. There were no necropsy or histopathology findings considered to be related to fentanyl treatment. There were no gross or microscopic evidence of abnormalities at the skin application site. There were no gross or microscopic evidence of abnormalities in the eyes of the four canines in the 3× and 5× groups that were observed with lens opacities over the first 7 days of the study.

TABLE 17

Mean red blood cell and platelet parameters by dose group (n = 6 per group) vs. time.

| Parameter | Day | Control | 1X | 3X | 5X |
|---|---|---|---|---|---|
| Red blood cells | −7 | 6.34 | 6.45 | 6.42 | 6.17 |
| ($10^6$/μL) | 3 | 5.91 | 6.55 | 6.76 | 6.30 |
| | 14 | 5.67 | 5.54 | 5.59 | 5.07 |
| Hemoglobin | −7 | 14.7 | 15.0 | 15.1 | 14.4 |
| (g/dL) | 3 | 13.6 | 15.2 | 15.9 | 14.8 |
| | 14 | 12.8 | 12.6 | 12.8 | 11.6 |
| Hematocrit | −7 | 43.6 | 44.8 | 44.9 | 42.8 |
| (%) | 3 | 40.8 | 45.6 | 46.9 | 44.0 |
| | 14 | 38.7 | 38.0 | 38.4 | 34.7 |
| MCV | −7 | 68.8 | 69.5 | 69.9 | 69.5 |
| (fL) | 3 | 69.0 | 69.6 | 69.3 | 69.9 |
| | 14 | 68.2 | 68.7 | 68.8 | 68.5 |
| MCH | −7 | 23.1 | 23.3 | 23.5 | 23.3 |
| (pg) | 3 | 23.0 | 23.2 | 23.5 | 23.4 |
| | 14 | 22.6 | 22.7 | 23.0 | 22.8 |
| MCHC | −7 | 33.6 | 33.5 | 33.6 | 33.6 |
| (g/dL) | 3 | 33.3 | 33.4 | 33.8 | 33.6 |
| | 14 | 33.2 | 33.1 | 33.4 | 33.4 |
| Reticulocytes | −7 | 0.200 | 0.250 | 0.300 | 0.200 |
| (%) | 3 | 0.667 | 0.583 | 0.500 | 0.667 |
| | 14 | 0.783 | 0.667 | 1.067 | 1.050 |
| RDW | −7 | 14.0 | 13.6 | 13.6 | 13.2 |
| (%) | 3 | 14.1 | 13.5 | 13.6 | 13.2 |
| | 14 | 14.3 | 13.9 | 14.0 | 13.7 |
| Platelets | −7 | 404 | 363 | 433 | 383 |
| ($10^3$/μL) | 3 | 337 | 327 | 394 | 322 |
| | 14 | 328 | 292 | 367 | 313 |

MCV: Mean corpuscular volume;
MCH: Mean corpuscular hemoglobin;
MCHC: Mean corpuscular hemoglobin concentration;
RDW: Red cell distribution width.

TABLE 18

Mean white blood cell parameters by dose group (n = 6 per group) vs. time.

| Parameter | Day | Control | 1X | 3X | 5X |
|---|---|---|---|---|---|
| White Blood | −7 | 9.66 | 13.2 | 13.3 | 14.6 |
| Cells | 3 | 8.61 | 11.7 | 16.9 | 16.5 |
| ($10^3$/μL) | 14 | 7.96 | 8.02 | 10.6 | 13.0 |
| Neutrophils | −7 | 4.97 | 7.32 | 7.93 | 7.94 |
| ($10^3$/μL) | 3 | 3.97 | 7.24 | 12.1 | 12.5 |
| | 14 | 3.88 | 3.79 | 5.72 | 8.08 |
| Lymphocytes | −7 | 3.22 | 3.77 | 3.73 | 3.91 |
| ($10^3$/μL) | 3 | 3.21 | 3.09 | 3.12 | 2.50 |
| | 14 | 2.93 | 2.95 | 2.94 | 2.83 |
| Monocytes | −7 | 0.648 | 0.995 | 0.850 | 1.02 |
| ($10^3$/μL) | 3 | 0.510 | 0.653 | 0.923 | 0.743 |
| | 14 | 0.477 | 0.475 | 0.668 | 0.817 |
| Eosinophils | −7 | 0.670 | 0.900 | 0.617 | 1.49 |
| ($10^3$/μL) | 3 | 0.815 | 0.627 | 0.558 | 0.618 |
| | 14 | 0.585 | 0.750 | 1.15 | 1.15 |
| Basophils | −7 | 0.0683 | 0.0933 | 0.0767 | 0.103 |
| ($10^3$/μL) | 3 | 0.0467 | 0.0367 | 0.0667 | 0.0300 |
| | 14 | 0.0400 | 0.0283 | 0.0400 | 0.0317 |

TABLE 19

Mean serum chemistry parameters by dose group (n = 6 per group) vs. time.

| Parameter | Day | Control | 1X | 3X | 5X |
|---|---|---|---|---|---|
| Sodium | −7 | 149 | 149 | 149 | 150 |
| (mEq/L) | 3 | 147 | 148 | 147 | 148 |
| | 14 | 144 | 145 | 146 | 144 |
| Potassium | −7 | 5.13 | 5.12 | 5.52 | 5.18 |
| (mEq/L) | 3 | 4.92 | 4.92 | 4.52 | 4.60 |
| | 14 | 4.68 | 4.68 | 4.67 | 4.42 |
| Chloride | −7 | 115 | 114 | 115 | 115 |
| (mEq/L) | 3 | 115 | 113 | 106 | 112 |
| | 14 | 112 | 112 | 114 | 113 |
| Calcium | −7 | 11.1 | 11.1 | 11.1 | 11.1 |
| (mg/dL) | 3 | 10.9 | 10.9 | 11.1 | 10.9 |
| | 14 | 10.8 | 10.8 | 10.6 | 10.5 |
| Inorganic | −7 | 7.82 | 7.57 | 7.57 | 7.50 |
| Phosphorus | 3 | 8.02 | 7.67 | 7.82 | 7.17 |
| (mg/dL) | 14 | 7.63 | 7.23 | 6.88 | 6.68 |
| BUN | −7 | 7.00 | 7.00 | 7.00 | 8.17 |
| (mg/dL) | 3 | 6.17 | 8.50 | 14.2 | 13.2 |
| | 14 | 7.33 | 7.83 | 6.00 | 7.50 |
| Creatinine | −7 | 0.883 | 0.883 | 0.933 | 0.950 |
| (mg/dL) | 3 | 0.683 | 0.683 | 0.700 | 0.650 |
| | 14 | 0.867 | 0.850 | 0.850 | 0.900 |
| ALT | −7 | 21.2 | 19.0 | 18.5 | 20.3 |
| (IU/L) | 3 | 24.7 | 22.8 | 18.7 | 18.8 |
| | 14 | 23.0 | 22.5 | 24.7 | 21.5 |
| AST | −7 | 16.3 | 17.2 | 17.7 | 20.3 |
| (IU/L) | 3 | 17.7 | 16.8 | 13.7 | 10.7 |
| | 14 | 17.0 | 16.7 | 18.0 | 17.2 |
| ALP | −7 | 142 | 120 | 125 | 122 |
| (IU/L) | 3 | 146 | 135 | 131 | 127 |
| | 14 | 144 | 125 | 123 | 100 |
| Total | −7 | 0.117 | 0.133 | 0.150 | 0.167 |
| Billirubin | 3 | 0.183 | 0.183 | 0.217 | 0.183 |
| (mg/dL) | 14 | 0.133 | 0.150 | 0.100 | 0.117 |
| GGT | −7 | 2.17 | 2.67 | 2.17 | 2.50 |
| (IU/L) | 3 | 1.83 | 2.00 | 1.83 | 2.33 |
| | 14 | 1.50 | 2.33 | 2.17 | 2.00 |
| CK | −7 | 207 | 216 | 198 | 228 |
| (IU/L) | 3 | 217 | 255 | 278 | 256 |
| | 14 | 164 | 165 | 150 | 120 |
| Glucose | −7 | 114 | 112 | 117 | 107 |
| (mg/dL) | 3 | 118 | 117 | 124 | 137 |
| | 14 | 120 | 116 | 116 | 115 |
| Total | −7 | 5.58 | 5.62 | 5.63 | 5.53 |
| Protein | 3 | 5.48 | 5.68 | 5.92 | 5.63 |
| (g/dL) | 14 | 5.53 | 5.40 | 5.12 | 5.12 |
| Albumin | −7 | 2.70 | 2.77 | 2.77 | 2.63 |
| (g/dL) | 3 | 2.75 | 2.90 | 2.88 | 2.72 |
| | 14 | 2.78 | 2.77 | 2.57 | 2.38 |

TABLE 19-continued

Mean serum chemistry parameters by dose group (n = 6 per group) vs. time.

| Parameter | Day | Control | 1X | 3X | 5X |
|---|---|---|---|---|---|
| Globulin (g/dL) | -7 | 2.88 | 2.85 | 2.87 | 2.90 |
|  | 3 | 2.73 | 2.78 | 3.03 | 2.92 |
|  | 14 | 2.75 | 2.63 | 2.55 | 2.73 |
|  | 3 | 1.02 | 1.05 | 0.967 | 0.933 |
|  | 14 | 1.02 | 1.05 | 1.00 | 0.900 |
| Cholesterol (mg/dL) | -7 | 169 | 175 | 198 | 182 |
|  | 3 | 167 | 169 | 226 | 200 |
|  | 14 | 161 | 161 | 173 | 176 |

BUN: Blood urea nitrogen;
ALT: Alanine aminotransferase;
AST: Aspartate aminotransferase;
ALP: Alkaline phosphatase;
GGT: Gamma glutamyltransferase;
CK: Creatine phosphokinase;
A/G: Albumin to globulin ratio Adverse reactions in the 1× group were transient and included a low incidence of mild sedation, reduced food intake, modest weight loss and minimal reductions in heart rate and rectal temperature. Moderate to severe sedation emerged in the 3× and 5× groups that was associated with a dose limiting reduction in food and water intake, necessitating maintenance fluid replacement for the first two days following application. Also observed in the higher dose groups were an increased incidence of abnormal stools and transient lens opacities.

Sedation is an expected extension of the pharmacological effect of opioids. Mild sedation was observed sporadically in some canines in the 1× dose group over 48 hours and with a greater magnitude and duration in the 3× and 5× groups. These observations are consistent with previous reports where sedation increased with plasma fentanyl concentrations when parenterally administered. Sedation has been reported in canines following fentanyl transdermal patch application as well when used at the recommended dose. At the higher doses of the composition of the present invention (i.e., 3× and 5×) used in this study, sedation was a dose limiting adverse event in that it resulted in lack of food and water intake requiring maintenance fluid replacement over 2 days. This was unlikely the result of nausea as the emesis rate was no different in placebo- and fentanyl-treated canines. In the 5× group, food intake was eliminated altogether over 48 hours with a gradual return to baseline over 7 days. Food intake was sufficiently suppressed to cause a modest decrease in mean bodyweight. Inappetence has been described with fentanyl administration and the reduction in food intake may be a direct result of the drug, independent of sedation. A surgical standard of care is that canines are typically fasted prior to surgery and are gradually offered increasing quantities of food over time post-operatively depending on the disease that necessitated surgery. Fentanyl-induced reduced food intake may be superimposed on these post-operative care practices resulting in an under awareness of this outcome.

The reversible bilateral lens opacities observed in one 3× and three 5× group canines on Days 3 and 7 were likely due to corneal drying caused by prolonged moderate to severe sedation. Although not reported in canines, this change has been observed in rats that were anesthetized or that had corneal drying for any reason. In such cases, the lens fibers along the posterior suture swell because of slight osmotic changes in the cornea which somehow affect the aqueous and ultimately the lens. These changes are not cataracts because they are reversible. However, the changes can become irreversible if the condition(s) causing corneal drying are left unchecked. It was therefore considered likely that the extended sedation associated with 3× and 5× dosing in the present study resulted in transient corneal and lens drying, which in turn caused the reversible lens opacities. These conclusions are also supported by the lack of histopathologic findings in the lens. Although not observed in the 1× group, a prudent clinical practice is to use eye lubrication for a period of time until the normal palpebral reflex has been established following anesthesia.

Hypoventilation and respiratory depression were not dose limiting adverse reactions in this study. This adverse event has been described in humans in association with patch-delivered fentanyl that has resulted in acute death. As a result, transdermal patches are contraindicated for use in conjunction with surgery and necessitate prior tolerance to opioids. This is clearly not the case with administration of the composition of the present invention in canines. Reductions in respiratory rates were transient and marginally dose-dependent with a maximum reduction in rate of approximately 30% in the 3× and 5× groups over the first 48 hours. These observations are further supported by fentanyl data in canines following injection and patch transdermal delivery. Plasma fentanyl concentrations as high as approximately 80 ng/mL reduce the respiratory rate by only approximately 11 breaths/minute (50%) in spontaneously breathing canines. Additionally, respiratory rate, oxygen consumption, and blood gases ($pCO_2$, $pO_2$, and pH) do not change further as concentrations increase above 100 ng/mL. Sustained steady-state plasma fentanyl concentrations of approximately 2 ng/mL as delivered by a patch over 48 hours do not cause postoperative hypoventilation a confirmed by blood gas analysis. When taken together, there is no data to support the necessity of prior opioid tolerance or contraindication with anesthesia for use of the composition of the present invention in canines.

Mean heart rates decreased in a dose-dependent manner following administration of the composition of the present invention. Reduced heart rates have been reported with both parenteral and patch delivered fentanyl. At plasma fentanyl concentrations of 15 ng/mL, heart rates decreased by approximately 35 beats/minute (50%) and further decreases in heart rate were not observed when plasma fentanyl concentrations exceeded 15 ng/mL. The mean $C_{max}$ in the 5× group was 13.5 ng/mL and the maximum drop in heart rate was approximately 50% at 24 hours following dose application. There were no changes to cardiac indices nor were arrhythmias observed in the present study consistent with previous reports.

Although reduced rectal temperature is discussed in general terms in the opioid literature for canines, body temperature outcomes in conscious canines over time have not been reported following fentanyl administration. Opioids appear to alter the equilibrium point of the hypothalamic heat-regulatory mechanism resulting in reduced body temperature. The mean rectal body temperatures in this study decreased in a dose-dependent manner. In the 1× dose, a transient decrease in body temperature was observed with a maximum drop of 2° C. at 24 hours following dosing. In anesthetized canines, mean rectal temperatures decreased 0.9° C. 60 minutes into mastectomy when an administered 5 µg/kg/minute CRI of fentanyl throughout surgery, an infusion rate that overlaps with the 1× dose and was no different than placebo.

The appearance of abnormal feces that included discolored stools (dark or red), diarrhea or mucoid feces increased with the dose of the composition of the present invention over the 14 day study period. Abnormal feces in the 1× group was infrequent and limited to Days 1-3 whereas in the 3× and 5× groups, abnormal feces were more sporadic beginning at Day 4 through the end of the study. Opioids have been reported to diminish small intestinal secretions and decrease colonic propulsive peristaltic waves resulting in reduced, desiccated feces. The appearance of loose, mucoid or dark stools later in the study in the 3× and 5× groups may be related to this phenomenon or may be related to a return to feeding after marked food reduction.

All mean clinical pathology results remained within the normal range throughout the study although the mean BUN on Day 3 in both the 3× and 5× groups increased slightly from baseline. Creatinine did not show an increase in parallel with BUN and there were no gross or histological lesions in the kidneys. This was most likely associated with reduced water intake secondary to sedation that necessitated fluid replacement. Simultaneous urine samples were not collected to confirm a pre-renal association. Alternate possibilities are reduced urine output secondary to the release of antidiuretic hormone (ADH). High doses of fentanyl have been shown to have antidiuretic properties in the canine and are likely related to the release of ADH.

All abnormal health observations were completely resolved prior to necropsy on Day 14 and there were no histological abnormalities identified. These data support the safe use of the 1× dose and describe the outcome of an overdose of up to 5× the dose in the absence of opioid reversal.

In summary, the results from Example 6 demonstrate the margin of safety of administration of the composition of the present invention in healthy, laboratory canines when administered at 1×, 3× and 5× the proposed dose of 2.6 mg/kg (50 µL/kg).

EXAMPLE 7

Naloxone Reversal of the Narcotic Effects of an Overdose of a Fentanyl Composition Administered to Canines An intramuscular (IM) naloxone reversal regime to the narcotic side-effects of an overdose of the composition of the present invention in canines can be evaluated. Twenty-four healthy purpose bred laboratory beagle canines (12 males/12 females) were administered a single 13 mg/kg dose (5× overdose) of the composition of the present invention and randomized to 2 reversal regime treatment groups, 40 µg/kg (8 canines) or 160 µg/kg IM naloxone (16 canines). All canines were administered a single approximately 5× (13.0 mg/kg) overdose of the composition of the present invention (use dose of 2.7 mg/kg) to the ventral abdomen. Sixteen hours after administration of the composition of the present invention, canines were administered 8 hourly IM naloxone administrations according to their treatment assignment. All canines were sedated prior to naloxone administration.

The plasma naloxone and fentanyl concentrations are displayed in Table 20. Plasma fentanyl concentrations were below the LLOQ prior to dosing in all canines and the mean fentanyl concentrations ranged from 4.60 to 6.53 ng/ml across both groups from 16 through 24 hours following administration of a 5× overdose (13 mg/kg) of the composition of the present invention. The plasma naloxone concentrations were also below the LLOQ prior to IM naloxone dose administration in all canines. At 5 minutes following the fifth naloxone dose administration (20.083 hr), the plasma naloxone concentrations were 10.4±0.238 ng/ml and 34.7±1.75 ng/ml in the 40 and 160 µg/kg IM naloxone dose groups (Group 1 and 2), respectively. At 24 hours, the mean plasma naloxone concentrations had dropped substantially from the previous peaks in both groups, consistent with its known short duration of action and rapid clearance. No seizures or other adverse affects of naloxone administration were observed in any canines.

TABLE 20

Plasma fentanyl and naloxone concentrations by IM naloxone treatment group

| | Plasma Fentanyl Conc. (ng/mL) | | | | Plasma Naloxone Conc. (ng/mL) | | | |
|---|---|---|---|---|---|---|---|---|
| | 40 µg/kg IM Naloxone | | 160 µg/kg IM Naloxone | | 40 µg/kg IM Naloxone | | 160 µg/kg IM Naloxone | |
| Time (hr) | Mean | SD | Mean | SD | Mean | SD | Mean | SD |
| 0 | <LLOQ | — | <LLOQ | — | <LLOQ | — | <LLOQ | — |
| 16 | 4.60 | 1.52 | 5.46 | 1.18 | <LLOQ | — | <LLOQ | — |
| 20.083 | 5.92 | 2.47 | 5.80 | 1.43 | 10.4 | 0.672 | 34.7 | 7.02 |
| 24 | 5.42 | 2.60 | 6.53 | 2.27 | 2.78 | 0.568 | 12.8 | 3.39 |

SD: Standard deviation;
< LLOQ: Less than lower limit of quantification for all subjects.

For unknown reasons, six canines were observed as sedated at the time of administration of the composition of the present invention (0 hr). Following a 5× overdose (13 mg/kg) of the composition of the present invention, all canines were sedated prior to naloxone administration (i.e. at 14, 15, 15.917 hr). The administration of either 40 or 160 µg/kg IM naloxone at hourly intervals reduced the proportion of sedated canines. The mean proportion of sedated canines from 16 through 24 hours for group 1 and 2 was 0.698 and 0.438, respectively. Additionally, all canines were determined to be sedated at least once from 16 through 24 hours in both groups. The mean proportion of sedated canines returned to 1.0 following cessation of the hourly IM naloxone administrations for both groups by 26 hours.

The overall effect of naloxone on reversal of the sedative effects of the composition of the present invention was statistically significant (P<0.001), as was the individual effect of the 40 and 160 µg/kg IM naloxone reversal regimes (P<0.001 for both regimes). The analysis also indicated that there was significant subject-to-subject variability in the sedation response (i.e. the probability that $\sigma^2 > 0$ was <0.05). Furthermore, the narcotic reversal affect of the 160 µg/kg IM naloxone dose was significantly greater than that for the 40 µg/kg IM naloxone dose (P=0.0132). The odds of a subject being sedated with a 160 µg/kg IM naloxone dose was 0.353 (95% CI [0.0327-0.674]) fold that of a 40 µg/kg IM naloxone dose. Due to high degree of correlation (near −1.00) between $\beta_F$ and $\beta_N{}^{40}$, $\beta_N{}^{160}$, the value of $\beta_F$ was fixed to the initial estimate of 11.5. Varying the fixed value of $\beta_F$ from 1 to 30 had no affect on the hypothesis test results (accurate numerical integration of the likelihood could not be achieved for values of $\beta_F$>30), indicating the results are robust to different reasonable fixed values of $\beta_F$.

The rectal body temperatures across both groups dropped from 38.4±0.0976° C. prior to administration of the composition of the present invention to 35.1±0.0884° C. following treatment (i.e. at time 14, 15, and 15.917 hr). During IM naloxone reversal (i.e. from 16 through 24 hr), the body temperature across both groups was 37.7±0.0578° C. By 26 and 28 hours the body temperatures returned to near pre-naloxone administration values with an overall mean of 35.9±0.0976° C. The mean body temperature during naloxone treatment time period ($\mu_N$) was 2.19±0.0638° C. higher than the mean during the fentanyl only time period ($\mu_F$) (P<0.001). Additionally, during the naloxone treatment time period the body temperature was 0.412±0.123° C. higher in the 160 µg/kg IM naloxone dose group than in the 40 µg/kg IM naloxone dose group (P<0.001), indicating greater narcotic reversal effect of the higher IM naloxone dose.

The heart rates, across both groups dropped from 101±3.31 bpm prior to administration of the composition of the present invention to 64.2±3.04 bpm following administration of the composition (i.e. at time 14, 15, and 15.917 hr). During IM naloxone reversal (i.e. from 16 through 24 hr), the HR across both groups returned to the pre-administration HR measurements with a value of 101±2.41 bpm, and then dropped again to an overall mean of 83.1±3.31 bpm following termination of naloxone administration. The mean HR during naloxone treatment time period ($\mu_N$) was 28.9±1.78 bpm higher than the mean during the fentanyl only time period ($\mu_F$) (P<0.001). Finally, during the naloxone treatment time period the HR was 9.97±5.11 bpm higher in the 160 µg/kg IM naloxone dose group than in the 40 µg/kg IM naloxone dose group (P=0.0258), further indicating greater narcotic reversal effect of the 160 µg/kg IM naloxone dosage.

In summary, the narcotic side-effects of an overdose of the composition of the present invention can be safely and effectively reversed by hourly administration of either 40 µg/kg or 160 µg/kg IM naloxone; however, the 160 µg/kg regime is more effective.

EXAMPLE 8

In Vitro and In Vivo Effect of Penetration Enhancer Following Transdermal Administration of a Fentanyl Composition to Canines The in vitro and in vivo effects of the penetration enhancer in the composition of the present invention can be evaluated. In vitro effects can be assessed by applying a fentanyl composition with a penetration enhancer and a fentanyl composition without a penetration enhancer to cadaver skin. Thereafter, the effect of fentanyl flux across the skin can be evaluated. In this experiment, octyl salicylate can be used as the penetration enhancer. In vivo effects can be assessed by administering a single dose of the fentanyl composition with a penetration enhancer and a single dose of the fentanyl composition without a penetration enhancer to canines at a dorsal location. Thereafter, the systemic blood level exposure of fentanyl in the canines can be evaluated. In this experiment, octyl salicylate can be used as the penetration enhancer.

In the in vivo experiment, Group 1 included twelve adult male beagle dogs administered a single transdermal dose of a composition comprising fentanyl at a concentration of 2.6 mg/kg (52 µL/kg) plus octyl salicylate. A second group (Group 2) included twelve adult male beagle dogs administered a single transdermal dose of a composition comprising fentanyl at a concentration of 2.6 mg/kg (52 µL/kg) but without octyl salicylate.

Blood samples for plasma fentanyl concentration determination were collected from pre-dosing through 21 days post-dosing from all subjects. A deconvolution analysis was conducted to determine the systemic absorption of fentanyl over time, and the cumulative amount of fentanyl systemically absorbed at 21 days post-dosing was statistically compared between the two treatment groups.

The summary statistics of the systemic fentanyl absorption rates for the two treatment groups are displayed in Table 21. The mean systemic absorption rate was greater in Group 1 than Group 2 at each sampling time point through 96 hours post-dosing, indicating a substantial effect of octyl salicylate on the fentanyl absorption rate for the first 96 hours after transdermal fentanyl solution administration. After 96 hours post-dosing, the systemic fentanyl absorption rates were similar in both treatment groups.

TABLE 21

Systemic fentanyl absorption rate (mg/kg/hr) summary statistics by treatment group and time

| | | Time (hours) | | | | | | | | |
|---|---|---|---|---|---|---|---|---|---|---|
| | | 0 | 1 | 2 | 4 | 8 | 12 | 16 | 24 | 36 |
| Group 1 | n | 12 | 12 | 12 | 12 | 12 | 12 | 12 | 12 | 12 |
| | Mean | 0.00 | 0.00643 | 0.00302 | 0.00898 | 0.0233 | 0.00421 | 0.00872 | 0.00767 | 0.00754 |
| | SD | 0.00 | 0.00756 | 0.00255 | 0.00700 | 0.0226 | 0.00380 | 0.00236 | 0.00283 | 0.00269 |
| Group 2 | n | 12 | 12 | 12 | 12 | 12 | 12 | 12 | 12 | 12 |
| | Mean | 0.00 | 0.00319 | 0.00163 | 0.00430 | 0.0140 | 0.00108 | 0.00377 | 0.00401 | 0.00218 |
| | SD | 0.00 | 0.00238 | 0.00186 | 0.00456 | 0.0157 | 0.00121 | 0.00294 | 0.00376 | 0.00111 |

| | | Time (hours) | | | | | | |
|---|---|---|---|---|---|---|---|---|
| | | 48 | 96 | 168 | 240 | 336 | 408 | 504 |
| Group 1 | n | 12 | 12 | 12 | 12 | 12 | 12 | 12 |
| | Mean | 0.00736 | 0.00501 | 0.00251 | 0.00162 | 0.00127 | 0.000801 | 0.000667 |
| | SD | 0.00335 | 0.00331 | 0.00226 | 0.000436 | 0.000784 | 0.000480 | 0.000642 |
| Group 2 | n | 12 | 12 | 12 | 12 | 12 | 12 | 12 |
| | Mean | 0.00353 | 0.00266 | 0.00263 | 0.00184 | 0.00148 | 0.000935 | 0.000629 |
| | SD | 0.00189 | 0.00105 | 0.00131 | 0.000741 | 0.000543 | 0.000360 | 0.000441 |

SD: Standard Deviation

The summary statistics of the cumulative systemic fentanyl absorption for the two treatment groups are displayed in Table 22. The cumulative systemic absorption at 48 hours post-dosing were 0.413±0.168 (mean±SD) and 0.193±0.0943 mg/kg in Group 1 and Group 2, respectively. Similarly, the cumulative systemic absorption amounts at 96 hours post-dosing were 0.706±0.272 and 0.342±0.126 mg/kg in Group 1 and Group 2, respectively. Thus, at 48 and 96 hours post-dosing, over twice as much fentanyl was systemically absorbed in dogs administered transdermal fentanyl solution containing octyl salicylate than in dogs administered transdermal fentanyl solution without octyl salicylate. At 21 days (504 hours) post-dosing the cumulative systemic absorption was 1.40-fold higher in Group 1 than in Group 2 at 1.41±0.550 and 1.01±0.260 mg/kg, respectively. This difference in cumulative systemic absorption was statistically significant (P<0.05).

TABLE 22

Cumulative systemic fentanyl absorption (mg/kg) summary statistics by treatment group and time

|  |  | Time (hours) | | | | | | | |
| --- | --- | --- | --- | --- | --- | --- | --- | --- | --- |
|  |  | 0 | 1 | 2 | 4 | 8 | 12 | 16 | 24 |
| Group 1 | n | 12 | 12 | 12 | 12 | 12 | 12 | 12 | 12 |
|  | Mean | 0.00 | 0.00122 | 0.00793 | 0.0189 | 0.0845 | 0.142 | 0.166 | 0.233 |
|  | SD | 0.00 | 0.00135 | 0.00430 | 0.00865 | 0.0631 | 0.107 | 0.106 | 0.119 |
| Group 2 | n | 12 | 12 | 12 | 12 | 12 | 12 | 12 | 12 |
|  | Mean | 0.00 | 0.00655 | 0.00871 | 0.0133 | 0.0503 | 0.0810 | 0.0901 | 0.122 |
|  | SD | 0.00 | 0.0130 | 0.0125 | 0.0120 | 0.0419 | 0.0714 | 0.0714 | 0.0757 |

|  |  | Time (hours) | | | | | | | |
| --- | --- | --- | --- | --- | --- | --- | --- | --- | --- |
|  |  | 36 | 48 | 96 | 168 | 240 | 336 | 408 | 504 |
| Group 1 | n | 12 | 12 | 12 | 12 | 12 | 12 | 12 | 12 |
|  | Mean | 0.323 | 0.413 | 0.706 | 0.985 | 1.13 | 1.26 | 1.34 | 1.41 |
|  | SD | 0.143 | 0.168 | 0.272 | 0.458 | 0.527 | 0.537 | 0.545 | 0.550 |
| Group 2 | n | 12 | 12 | 12 | 12 | 12 | 12 | 12 | 12 |
|  | Mean | 0.159 | 0.193 | 0.342 | 0.533 | 0.694 | 0.853 | 0.940 | 1.01 |
|  | SD | 0.0848 | 0.0943 | 0.126 | 0.160 | 0.199 | 0.221 | 0.240 | 0.260 |

SD: Standard Deviation

In summary, the mean systemic fentanyl absorption rates were greater through 96 hours post-dosing in dogs that received transdermal fentanyl solution containing octyl salicylate than in dogs that received transdermal fentanyl solution without octyl salicylate. Likewise, at 21 days post-dosing, the mean cumulative amount of systemically absorbed fentanyl was 1.40-fold higher (P<0.05) in dogs that received the transdermal fentanyl solution containing octyl salicylate. Thus, the penetration enhancer octyl salicylate increased both the rate and extent of systemic fentanyl absorption following a single topical administration of transdermal fentanyl solution to the dorsal inter-scapular region in dogs.

EXAMPLE 9

Effect of Wetting on the Amount of Topical Residual Fentanyl Wiped from the Application Site Following Transdermal Administration of a Fentanyl Composition to Canines The effects of wetting the application site in canines following transdermal administration of the composition of the present invention can be evaluated. The evaluation can be performed by measuring the amount of residual fentanyl wiped from the topical application site of canines following a single administration of the composition of the present invention. Canines can be randomized to 1 of 10 treatment groups (4 canines per group). The application site (dorsal, inter-scapular region) of all canines can be wiped with a cotton glove on Day −1 to confirm that no fentanyl is present prior to dose administration. Canines in five of the treatment groups (i.e., Groups 1W-5W) can have the application site wetted with distilled water (via a spray bottle) approximately 5 minutes prior to cotton glove wiping. Canines in the other five treatment groups (i.e., Groups 1D-5D) can have the application site remain dry prior to cotton glove wiping. A single approximately 2.7 mg/kg (~54 µL/kg) topical dose of the composition of the present invention can be applied to the dorsal, interscapular region to all canines on Day 0. A second cotton glove wiping (wet or dry) can be conducted for each canine post-dosing according to the treatment randomization. Groups 1D and 1W canines can be wiped on Day 0 at 8 hours post-dose administration. Canines in Groups 2D/W, 3D/W, 4D/W, and 5D/W can be wiped at 24, 48, 72, and 120 hours postdose administration, respectively. Cotton gloves can be assayed for fentanyl amounts using a validated analytical method. Summary statistics of the residual fentanyl amounts per glove, normalized for bodyweight, can be calculated by time and dry/wet application site. The effect of wetting the application site on the normalized residual fentanyl amounts can also be analyzed.

In the present example, 40 beagle canines were randomized to one of the ten treatment groups (4 canines per group). Table 23 shows the residual fentanyl amount (µg/kg of bodyweight) detected on cotton gloves for each treatment group. Fentanyl was not measurable (i.e., measurements were below the lower limit of quantification) on any of the pre-dose administration (Day −1) cotton glove samples. At 8 hours post-dosing, the mean residual fentanyl amounts recovered from the cotton gloves were 41.0 and 35.4 µg/kg of bodyweight with dry and wet application sites, respectively. As a percent of the nominal 2.7 mg/kg transdermal fentanyl solution dose, the mean residual fentanyl amounts were 1.52% and 1.31%, respectively. At 72 hours post-dosing, mean cotton glove residual amounts were 0.31% and 0.35% of the applied dose for dry and wet application sites, respectively; and at 120 hours post-dosing, the mean residual amounts were <0.28% and 0.19%, respectively.

TABLE 23

Residual fentanyl amount (µg/kg of body weight) detected on cotton gloves by nominal wiping time and dry or wet application site

| Application Site | | Time Post-Dosing (hours) | | | | | |
|---|---|---|---|---|---|---|---|
| | | 0 | 8 | 21 | 48 | 72 | 120 |
| Dry | N | 20 | 4 | 4 | 4 | 4 | 4 |
| | Mean | <LLOQ | 41.0 | 20.7 | 20.4 | 8.46 | <7.50 |
| | SD | NC | 12.1 | 6.87 | 6.11 | 2.31 | 4.80 |
| Wet | N | 20 | 4 | 4 | 4 | 4 | 4 |
| | Mean | <LLOQ | 35.4 | 15.2 | 20.5 | 9.49 | 5.12 |
| | SD | NC | 21.5 | 9.11 | 15.8 | 4.56 | 1.98 |

<LLOQ: less than the lower limit of quantification (20 µg);
NC: not calculable
SD: Standard Deviation A linear fixed effects model analysis indicated no statistically significant main effect of the dry versus wet application site on residual fentanyl amounts (p=0.4568) and no statistically significant interaction effect between the dry/wet application site and time post-dosing (p=0.9485). Thus, it appears that wetting the application site had no effect on the amount of topical residual fentanyl wiped from the application site with a cotton glove following a single administration of transdermal fentanyl solution to canines.

No animals were removed and no deaths occurred during the study. Seven adverse events occurred during the study. All adverse events occurred on Day 1 or 2 of the study and involved vomiting or vomiting and inappetance. The adverse events were categorized as mild and possibly related to fentanyl treatment. No medical interventions were required.

The invention claimed is:

1. A method of controlling pain for an effective period of time comprising transdermally administering to a canine in need thereof a therapeutically effective amount of a composition comprising fentanyl, a penetration enhancer, and a volatile liquid, wherein the composition is a solution, and the transdermal administration is applied to a dorsal location of the canine.

2. The method of claim 1 wherein the composition is administered as a single dose.

3. The method of claim 1 wherein the effective period of time is at least about 96 hours.

4. A method of treating pain comprising transdermally administering to a canine in need of treatment a therapeutically effective amount of a composition comprising fentanyl, a penetration enhancer, and a volatile liquid,
wherein the composition is a solution and is administered as a single dose, and
wherein the single dose is effective for the treatment of pain for at least about 96 hours, and the transdermal administration is applied to a dorsal location of the canine.

5. The method of claim 4 wherein the transdermal administration is applied to the dorsal interscapular location of the canine.

6. The method of claim 1 wherein the penetration enhancer is octyl salicylate.

7. The method of claim 1 wherein the volatile liquid is isopropanol.

8. The method of claim 1 wherein the pain is associated with a surgery performed or to be performed on the canine.

9. The method of claim 8 wherein the surgery is an orthopedic surgery.

10. The method of claim 8 wherein the surgery is a soft tissue surgery.

11. The method of claim 8 wherein the composition is administered to the canine about 2 to about 4 hours prior to the surgery.

12. The method of claim 11 wherein the composition is administered as a single dose.

13. The method of claim 1 wherein the composition is administered as a single unit dose.

14. The method of claim 1 wherein the composition comprises about 0.1 to about 10% (w/v) of fentanyl, about 0.1 to about 10% (w/v) of the penetration enhancer, and about 80 to about 99.8% (w/v) of the volatile liquid.

15. The method of claim 1 wherein the composition comprises about 3 to about 7% (w/v) of fentanyl, about 3 to about 7% (w/v) of the penetration enhancer, and about 86 to about 94% (w/v) of the volatile liquid.

16. The method of claim 1 wherein the composition comprises about 5% (w/v) of fentanyl, about 5% (w/v) of the penetration enhancer, and about 90% (w/v) of the volatile liquid.

17. The method of claim 16 wherein the penetration enhancer is octyl salicylate and the volatile liquid is isopropanol.

18. The method of claim 1 wherein the fentanyl is administered at a dose of about 0.1 to about 10 mg/kg of weight of the canine.

19. The method of claim 1 wherein the fentanyl is administered at a dose of about 1 to about 5 mg/kg of weight of the canine.

20. The method of claim 1 wherein the fentanyl is administered at a dose of about 2.7 mg/kg of weight of the canine.

21. The method of claim 1 wherein the composition is administered with one or more other therapeutic ingredients.

22. The method of claim 1 wherein the composition is administered using a transdermal dispensing apparatus.

23. The method of claim 1 wherein said dorsal location is the dorsal interscapular location.

24. The method of claim 4 wherein the pain is associated with a surgery performed or to be performed on the canine.

25. The method of claim 24 wherein the surgery is an orthopedic surgery.

26. The method of claim 24 wherein the surgery is a soft tissue surgery.

27. The method of claim 24 wherein the composition is administered to the canine about 2 to about 4 hours prior to the surgery.

28. The method of claim 4 wherein the composition comprises about 0.1 to about 10% (w/v) of fentanyl, about 0.1 to about 10% (w/v) of the penetration enhancer, and about 80 to about 99.8% (w/v) of the volatile liquid.

29. The method of claim 4 wherein the composition comprises about 3 to about 7% (w/v) of fentanyl, about 3 to about 7% (w/v) of the penetration enhancer, and about 86 to about 94% (w/v) of the volatile liquid.

30. The method of claim 4 wherein the composition comprises about 5% (w/v) of fentanyl, about 5% (w/v) of the penetration enhancer, and about 90% (w/v) of the volatile liquid.

31. The method of claim 30 wherein the penetration enhancer is octyl salicylate and the volatile liquid is isopropanol.

32. The method of claim 4 wherein the fentanyl is administered at a dose of about 0.1 to about 10 mg/kg of weight of the canine.

33. The method of claim 4 wherein the fentanyl is administered at a dose of about 1 to about 5 mg/kg of weight of the canine.

34. The method of claim 4 wherein the fentanyl is administered at a dose of about 2.7 mg/kg of weight of the canine.

35. The method of claim 4 wherein the composition is administered with one or more other therapeutic ingredients.

36. The method of claim 4 wherein the composition is administered using a transdermal dispensing apparatus.

* * * * *